US011827890B1

(12) United States Patent
Bermudes

(10) Patent No.: US 11,827,890 B1
(45) Date of Patent: *Nov. 28, 2023

(54) BACTERIA CARRYING BACTERIOPHAGE AND PROTEASE INHIBITORS FOR THE TREATMENT OF DISORDERS AND METHODS OF TREATMENT

(71) Applicant: David Gordon Bermudes, Woodland Hills, CA (US)

(72) Inventor: David Gordon Bermudes, Woodland Hills, CA (US)

(*) Notice: Subject to any disclaimer, the term of this patent is extended or adjusted under 35 U.S.C. 154(b) by 929 days.

This patent is subject to a terminal disclaimer.

(21) Appl. No.: 16/708,152

(22) Filed: Dec. 9, 2019

Related U.S. Application Data

(60) Continuation of application No. 15/456,091, filed on Mar. 10, 2017, now Pat. No. 10,501,746, which is a division of application No. 14/180,766, filed on Feb. 14, 2014, now Pat. No. 9,593,339.

(60) Provisional application No. 61/764,577, filed on Feb. 14, 2013.

(51) Int. Cl.
| | | |
|---|---|---|
| *A61K 8/00* | (2006.01) | |
| *C12N 15/74* | (2006.01) | |
| *C07K 16/24* | (2006.01) | |
| *A61K 31/7105* | (2006.01) | |
| *A61K 31/713* | (2006.01) | |
| *A61K 39/395* | (2006.01) | |
| *A61K 38/55* | (2006.01) | |
| *A61K 39/00* | (2006.01) | |

(52) U.S. Cl.
CPC .......... *C12N 15/746* (2013.01); *A61K 31/713* (2013.01); *A61K 31/7105* (2013.01); *A61K 38/55* (2013.01); *A61K 39/39558* (2013.01); *C07K 16/241* (2013.01); *A61K 2039/505* (2013.01); *C07K 2317/76* (2013.01); *Y02A 50/30* (2018.01)

(58) Field of Classification Search
CPC .......... C12N 15/746; A61K 31/7105; A61K 31/713; A61K 38/55; A61K 39/39558; A61K 2039/505; C07K 16/241; C07K 2317/76; Y02A 50/30
See application file for complete search history.

(56) References Cited

U.S. PATENT DOCUMENTS

| | | |
|---|---|---|
| 4,436,727 A | 3/1984 | Ribi |
| 4,906,567 A | 3/1990 | Connelly |
| 5,021,234 A | 6/1991 | Ehrenfeld |
| 5,087,569 A | 2/1992 | Gabay et al. |
| 5,126,257 A | 6/1992 | Gabay et al. |
| 5,143,830 A | 9/1992 | Holland et al. |
| 5,223,409 A | 6/1993 | Ladner et al. |
| 5,281,530 A | 1/1994 | Sick et al. |
| 5,318,900 A | 6/1994 | Habuka et al. |
| 5,338,724 A | 8/1994 | Gabay et al. |
| 5,344,762 A | 9/1994 | Karapetian |
| 5,354,675 A | 10/1994 | Iida et al. |
| 5,399,490 A | 3/1995 | Balganesh et al. |
| 5,403,484 A | 4/1995 | Ladner et al. |
| 5,466,672 A | 11/1995 | Kushnaryov et al. |
| 5,506,139 A | 4/1996 | Loosmore et al. |
| 5,571,698 A | 11/1996 | Ladner et al. |
| 5,604,201 A | 2/1997 | Thomas et al. |
| 5,656,436 A | 8/1997 | Loosmore et al. |
| 5,665,353 A | 9/1997 | Loosmore et al. |
| 5,705,151 A | 1/1998 | Dow et al. |
| 5,712,369 A | 1/1998 | Old et al. |
| 5,824,538 A | 10/1998 | Branstrom et al. |
| 5,830,702 A | 11/1998 | Portnoy et al. |
| 5,837,500 A | 11/1998 | Ladner et al. |
| 5,869,302 A | 2/1999 | Loosmore et al. |
| 5,877,159 A | 3/1999 | Powell et al. |
| 5,935,573 A | 8/1999 | Loosmore et al. |
| 5,939,297 A | 8/1999 | Loosmore et al. |
| 5,945,102 A | 8/1999 | de Faire et al. |
| 5,958,406 A | 9/1999 | de Faire et al. |
| 5,962,430 A | 10/1999 | Loosmore et al. |
| 5,981,503 A | 11/1999 | Loosmore et al. |
| 5,997,881 A | 12/1999 | Powell et al. |
| 6,004,562 A | 12/1999 | Campagnari |
| 6,020,183 A | 2/2000 | Loosmore et al. |
| 6,022,855 A | 2/2000 | Thomas et al. |
| 6,025,342 A | 2/2000 | Loosmore et al. |
| 6,030,612 A | 2/2000 | de Faire et al. |
| 6,051,237 A | 4/2000 | Paterson |
| 6,080,849 A | 6/2000 | Bermudes et al. |
| 6,114,125 A | 9/2000 | Loosmore et al. |
| 6,143,551 A | 11/2000 | Goebel |
| 6,147,057 A | 11/2000 | Loosmore et al. |

(Continued)

FOREIGN PATENT DOCUMENTS

| | | |
|---|---|---|
| EP | 0973911 A1 | 1/2000 |
| EP | 1513924 A1 | 3/2005 |

(Continued)

OTHER PUBLICATIONS

Celiberto et al. "Isolation and Characterization of Potentially Probiotic Bacterial Strains from Mice: Proof of Concept for Personalized Probiotics." Nutrients. Nov. 2018; 10(11): 1684. (Year: 2018).*

(Continued)

*Primary Examiner* — Titilayo Moloye
(74) *Attorney, Agent, or Firm* — HOFFBERG & ASSOCIATES; Steven M. Hoffberg; Steven M Hoffberg

(57) ABSTRACT

The present invention uses co-expression of protease inhibitors and protease sensitive therapeutic agents including phage and phagemids delivering peptides, therapeutic antibodies, DNA and RNA-based therapeutics that results in treating inflammation of a variety of disorders including psoriasis, atopic dermatitis and inflammatory bowel disease. The invention also provides bacteria that inhibit the growth of intestinal parasites such as worms, and deliver siRNA or miRNA that have specific anti-parasitic effects that results in the reduction or elimination of the parasite.

19 Claims, 2 Drawing Sheets

Specification includes a Sequence Listing.

(56) References Cited

U.S. PATENT DOCUMENTS

| | | |
|---|---|---|
| 6,150,170 A | 11/2000 | Powell et al. |
| 6,153,580 A | 11/2000 | Loosmore et al. |
| 6,190,657 B1 | 2/2001 | Pawelek et al. |
| 6,207,156 B1 | 3/2001 | Kuchroo et al. |
| 6,245,892 B1 | 6/2001 | Oaks et al. |
| 6,251,406 B1 | 6/2001 | Haefliger et al. |
| 6,277,379 B1 | 8/2001 | Oaks et al. |
| 6,348,344 B1 | 2/2002 | Ayal-Hershkovitz et al. |
| 6,410,012 B1 | 6/2002 | Sizemore et al. |
| 6,447,777 B1 | 9/2002 | Terman et al. |
| 6,447,784 B1 | 9/2002 | Bermudes et al. |
| 6,475,482 B1 | 11/2002 | Bermudes et al. |
| 6,475,763 B1 | 11/2002 | Ayal-Hershkovitz et al. |
| 6,537,558 B2 | 3/2003 | Kaniga |
| 6,548,287 B1 | 4/2003 | Powell et al. |
| 6,605,286 B2 | 8/2003 | Steidler et al. |
| 6,605,697 B1 | 8/2003 | Kwon et al. |
| 6,638,912 B2 | 10/2003 | Bhatnagar et al. |
| 6,680,374 B2 | 1/2004 | Oaks et al. |
| 6,685,935 B1 | 2/2004 | Pawelek et al. |
| 6,743,893 B2 | 6/2004 | Engler et al. |
| 6,746,671 B2 | 6/2004 | Steidler et al. |
| 6,841,535 B2 | 1/2005 | Divita et al. |
| 6,863,894 B2 | 3/2005 | Bermudes et al. |
| 6,923,972 B2 | 8/2005 | Bermudes et al. |
| 6,962,696 B1 | 11/2005 | Bermudes et al. |
| 6,979,538 B2 | 12/2005 | Ladner et al. |
| 7,001,884 B2 | 2/2006 | Komiyama et al. |
| 7,033,991 B2 | 4/2006 | Lindberg et al. |
| 7,118,879 B2 | 10/2006 | Ladner et al. |
| 7,208,293 B2 | 4/2007 | Ladner et al. |
| 7,258,863 B2 | 8/2007 | Oaks et al. |
| 7,354,592 B2 | 4/2008 | Bermudes et al. |
| 7,358,084 B2 | 4/2008 | Kolkman |
| 7,390,646 B2 | 6/2008 | Andino-Pavlovsky et al. |
| 7,413,877 B2 | 8/2008 | Collier et al. |
| 7,452,531 B2 | 11/2008 | Bermudes et al. |
| 7,514,089 B2 | 4/2009 | Bermudes et al. |
| 7,569,547 B2 | 8/2009 | Lindberg et al. |
| 7,635,682 B2 | 12/2009 | Denmeade et al. |
| 7,691,599 B2 | 4/2010 | Rubin |
| 7,696,173 B2 | 4/2010 | Collier et al. |
| 7,718,618 B2 | 5/2010 | Gallo et al. |
| 7,776,823 B2 | 8/2010 | Gallo et al. |
| 7,846,678 B2 | 12/2010 | Pepe et al. |
| 7,850,970 B2 | 12/2010 | Shapiro |
| 7,887,794 B2 | 2/2011 | Luquet et al. |
| 7,893,007 B2 | 2/2011 | Ladner et al. |
| 7,943,754 B2 | 5/2011 | Bentwich et al. |
| 8,030,447 B2 | 10/2011 | Motin et al. |
| 8,128,922 B2 | 3/2012 | Wu et al. |
| 8,153,414 B2 | 4/2012 | Caplan et al. |
| 8,231,878 B2 | 7/2012 | Colonna et al. |
| 8,241,623 B1 | 8/2012 | Bermudes |
| 8,246,945 B2 | 8/2012 | Caplan et al. |
| 8,283,319 B2 | 10/2012 | Schulte et al. |
| 8,349,570 B2 | 1/2013 | Pepe et al. |
| 8,372,620 B2 | 2/2013 | Sibbesen et al. |
| 8,440,207 B2 | 5/2013 | Bermudes |
| 8,507,249 B2 | 8/2013 | Finlay et al. |
| 8,524,220 B1 | 9/2013 | Bermudes |
| 8,609,358 B2 | 12/2013 | Sebastian et al. |
| 8,623,350 B1 | 1/2014 | Bermudes |
| 8,633,305 B2 | 1/2014 | Shapiro |
| 8,647,642 B2 | 2/2014 | Bermudes |
| 8,685,392 B2 | 4/2014 | Helmerhorst et al. |
| 8,758,771 B2 | 6/2014 | Finlay et al. |
| 8,771,669 B1 | 7/2014 | Bermudes |
| 8,795,730 B2 | 8/2014 | Vachon |
| 8,815,251 B2 | 8/2014 | Caplan et al. |
| 8,951,992 B2 | 2/2015 | Nathan et al. |
| 8,956,859 B1 | 2/2015 | Bermudes |
| 8,981,061 B2 | 3/2015 | Colonna et al. |
| 9,068,187 B1 | 6/2015 | Bermudes |
| 9,187,523 B2 | 11/2015 | Motin et al. |
| 9,200,251 B1 | 12/2015 | Bermudes |
| 9,200,289 B1 | 12/2015 | Bermudes |
| 2001/0006642 A1 | 7/2001 | Steidler et al. |
| 2001/0009957 A1 | 7/2001 | Oaks et al. |
| 2001/0029043 A1 | 10/2001 | Haefliger et al. |
| 2002/0026655 A1 | 2/2002 | Bermudes et al. |
| 2002/0150881 A1 | 10/2002 | Ladner et al. |
| 2002/0197276 A1 | 12/2002 | Oaks et al. |
| 2003/0059400 A1 | 3/2003 | Szalay |
| 2003/0082219 A1 | 5/2003 | Warren et al. |
| 2003/0087827 A1 | 5/2003 | Lindberg et al. |
| 2003/0109026 A1 | 6/2003 | Bermudes et al. |
| 2003/0113293 A1 | 6/2003 | Bermudes et al. |
| 2003/0113717 A1 | 6/2003 | Ladner et al. |
| 2003/0165875 A1 | 9/2003 | Colonna et al. |
| 2003/0170276 A1 | 9/2003 | Bermudes et al. |
| 2003/0219722 A1 | 11/2003 | Ladner et al. |
| 2003/0219886 A1 | 11/2003 | Ladner et al. |
| 2004/0005539 A1 | 1/2004 | Ladner et al. |
| 2004/0023205 A1 | 2/2004 | Ladner et al. |
| 2004/0219169 A1 | 11/2004 | Bermudes et al. |
| 2004/0229338 A1 | 11/2004 | King |
| 2004/0234998 A1 | 11/2004 | Sibbesen et al. |
| 2005/0013822 A1 | 1/2005 | Oaks et al. |
| 2005/0036987 A1 | 2/2005 | Pawelek et al. |
| 2005/0063994 A1 | 3/2005 | Caplan et al. |
| 2005/0069532 A1 | 3/2005 | Weinrauch et al. |
| 2005/0079573 A1 | 4/2005 | Sibbesen |
| 2005/0106151 A1 | 5/2005 | Shapiro |
| 2005/0118193 A1 | 6/2005 | Andino-Pavlovsky et al. |
| 2005/0148504 A1 | 7/2005 | Katunuma et al. |
| 2005/0202535 A1 | 9/2005 | Collier et al. |
| 2005/0203007 A1 | 9/2005 | Komiyama et al. |
| 2005/0208033 A1 | 9/2005 | Francois-Marie et al. |
| 2005/0249706 A1 | 11/2005 | Bermudes et al. |
| 2005/0255088 A1 | 11/2005 | Bermudes et al. |
| 2005/0260670 A1 | 11/2005 | Colonna et al. |
| 2006/0084113 A1 | 4/2006 | Ladner et al. |
| 2006/0088910 A1 | 4/2006 | Nguyen |
| 2006/0229336 A1 | 10/2006 | Kazmierski et al. |
| 2006/0241050 A1 | 10/2006 | Cameron et al. |
| 2007/0009489 A1 | 1/2007 | Bermudes et al. |
| 2007/0037744 A1 | 2/2007 | Gallo et al. |
| 2007/0041997 A1 | 2/2007 | Finlay et al. |
| 2007/0065908 A1 | 3/2007 | Gallo et al. |
| 2007/0071773 A1 | 3/2007 | Hanski et al. |
| 2007/0192905 A1 | 8/2007 | Piller et al. |
| 2007/0254329 A1 | 11/2007 | Rubin |
| 2007/0259417 A1 | 11/2007 | Ladner et al. |
| 2007/0275423 A1 | 11/2007 | Sebastian et al. |
| 2007/0298012 A1 | 12/2007 | King et al. |
| 2008/0089862 A1 | 4/2008 | Benhar et al. |
| 2008/0124355 A1 | 5/2008 | Bermudes |
| 2008/0181892 A1 | 7/2008 | Ledbetter et al. |
| 2008/0261869 A1 | 10/2008 | Shapiro |
| 2008/0311081 A1 | 12/2008 | Fruehauf et al. |
| 2009/0011974 A1 | 1/2009 | Bocharov et al. |
| 2009/0069248 A1 | 3/2009 | Motin et al. |
| 2009/0081199 A1 | 3/2009 | Colonna et al. |
| 2009/0111160 A1 | 4/2009 | Collier et al. |
| 2009/0123426 A1 | 5/2009 | Li et al. |
| 2009/0162356 A1 | 6/2009 | Lookeren Campagne |
| 2009/0169517 A1 | 7/2009 | Bermudes et al. |
| 2009/0214506 A1 | 8/2009 | Hardy et al. |
| 2009/0234101 A1 | 9/2009 | Ladner et al. |
| 2009/0294288 A1 | 12/2009 | May et al. |
| 2009/0305296 A1 | 12/2009 | Bengtsson et al. |
| 2010/0022584 A1 | 1/2010 | Kenyon et al. |
| 2010/0135961 A1 | 6/2010 | Bermudes |
| 2010/0136048 A1 | 6/2010 | Bermudes |
| 2010/0137192 A1 | 6/2010 | Shapiro |
| 2010/0166802 A1 | 7/2010 | Caplan et al. |
| 2010/0247544 A1 | 9/2010 | Vachon |
| 2010/0278819 A1 | 11/2010 | Bossuyt et al. |
| 2010/0279923 A1 | 11/2010 | Schulte et al. |
| 2010/0286251 A1 | 11/2010 | Rubin |
| 2010/0305306 A1 | 12/2010 | Colonna et al. |
| 2010/0310560 A1 | 12/2010 | Colonna et al. |
| 2011/0021416 A1 | 1/2011 | Shapiro |

(56) References Cited

U.S. PATENT DOCUMENTS

| | | |
|---|---|---|
| 2011/0028397 A1 | 2/2011 | Tozser et al. |
| 2011/0038917 A1 | 2/2011 | Kappers et al. |
| 2011/0104146 A1 | 5/2011 | Faraday |
| 2011/0152176 A1 | 6/2011 | Horswill |
| 2011/0190234 A1 | 8/2011 | Nathan et al. |
| 2011/0195423 A1 | 8/2011 | Selinfreund et al. |
| 2011/0223241 A1 | 9/2011 | Tardi et al. |
| 2011/0287037 A1 | 11/2011 | Gentschev et al. |
| 2012/0045474 A1 | 2/2012 | Motin et al. |
| 2012/0064062 A1 | 3/2012 | Goguen et al. |
| 2012/0064572 A1 | 3/2012 | Finlay et al. |
| 2012/0071545 A1 | 3/2012 | Shapiro |
| 2012/0142080 A1 | 6/2012 | Bermudes |
| 2012/0142623 A1 | 6/2012 | Lagunoff et al. |
| 2012/0230976 A1 | 9/2012 | Helmerhorst et al. |
| 2012/0308575 A1 | 12/2012 | Guo et al. |
| 2013/0023472 A1 | 1/2013 | Bristow |
| 2013/0028901 A1 | 1/2013 | Colonna et al. |
| 2013/0102017 A1 | 4/2013 | Pfaendler et al. |
| 2013/0150559 A1 | 6/2013 | Colonna et al. |
| 2013/0171109 A1 | 7/2013 | Helmerhorst et al. |
| 2013/0196432 A1 | 8/2013 | Poehlmann et al. |
| 2014/0005108 A1 | 1/2014 | Bristow |
| 2014/0056841 A1 | 2/2014 | Vachon |
| 2014/0150134 A1 | 5/2014 | Li et al. |
| 2014/0194346 A1 | 7/2014 | Aebi et al. |
| 2014/0220661 A1 | 8/2014 | Bermudes |
| 2014/0234310 A1 | 8/2014 | Shapiro |
| 2014/0296480 A1 | 10/2014 | Sanchez Garcia et al. |
| 2014/0322790 A1 | 10/2014 | Sebastian et al. |
| 2014/0370036 A1 | 12/2014 | Shapiro |
| 2015/0004705 A1 | 1/2015 | Lu et al. |
| 2015/0017204 A1 | 1/2015 | Bermudes |
| 2015/0071957 A1 | 3/2015 | Kelly et al. |
| 2015/0139940 A1 | 5/2015 | Bermudez Humaran et al. |
| 2015/0184220 A1 | 7/2015 | Sebastian et al. |

FOREIGN PATENT DOCUMENTS

| | | |
|---|---|---|
| EP | 1655370 A1 | 5/2006 |
| WO | WO1996040238 | 12/1996 |
| WO | WO1997014782 | 4/1997 |
| WO | WO1999010014 | 3/1999 |
| WO | WO1999010485 | 3/1999 |
| WO | WO2000004919 | 2/2000 |
| WO | WO2001014579 | 3/2001 |
| WO | WO2001025397 | 4/2001 |
| WO | WO2002070645 | 9/2002 |
| WO | WO2003072125 | 9/2003 |
| WO | WO2003102168 | 12/2003 |
| WO | WO2004076484 A1 | 9/2004 |
| WO | WO2004103404 A1 | 12/2004 |
| WO | WO2005014618 A2 | 2/2005 |
| WO | WO2005018332 A1 | 3/2005 |
| WO | WO2005054477 A1 | 6/2005 |
| WO | WO2006010070 A2 | 1/2006 |
| WO | WO2006048344 A1 | 5/2006 |
| WO | WO2006116545 A2 | 11/2006 |
| WO | WO2007083193 A2 | 7/2007 |
| WO | WO2008073148 A2 | 6/2008 |
| WO | WO2008091375 A2 | 7/2008 |
| WO | WO2008156702 A2 | 12/2008 |
| WO | WO2009006450 A1 | 1/2009 |
| WO | WO2009006453 A2 | 1/2009 |
| WO | WO2009014650 A2 | 1/2009 |
| WO | WO20090075898 | 6/2009 |
| WO | WO2009086116 A2 | 7/2009 |
| WO | WO2009126189 A1 | 10/2009 |
| WO | WO2009139985 A2 | 11/2009 |
| WO | WO2009152480 A2 | 12/2009 |
| WO | WO2010036391 A2 | 4/2010 |
| WO | WO2010057009 A1 | 5/2010 |
| WO | WO2011017137 A2 | 2/2011 |
| WO | WO2011086172 A1 | 7/2011 |

OTHER PUBLICATIONS

Longhi et al. "Microbiota and Cancer: The Emerging Beneficial Role of Bifidobacteria in Cancer Immunotherapy." Front Microbiol. 2020; 11: 575072. (Year: 2020).*

Kang et al. "Bacteria and bacterial derivatives as delivery carriers for immunotherapy." Adv Drug Deliv Rev. Feb. 2022;181:114085. (Year: 2022).*

Hwang et al. "Engineering commensal bacteria to rewire host-microbiome interactions." Curr Opin Biotechnol. Apr. 2020;62:116-122. (Year: 2020).*

\* cited by examiner

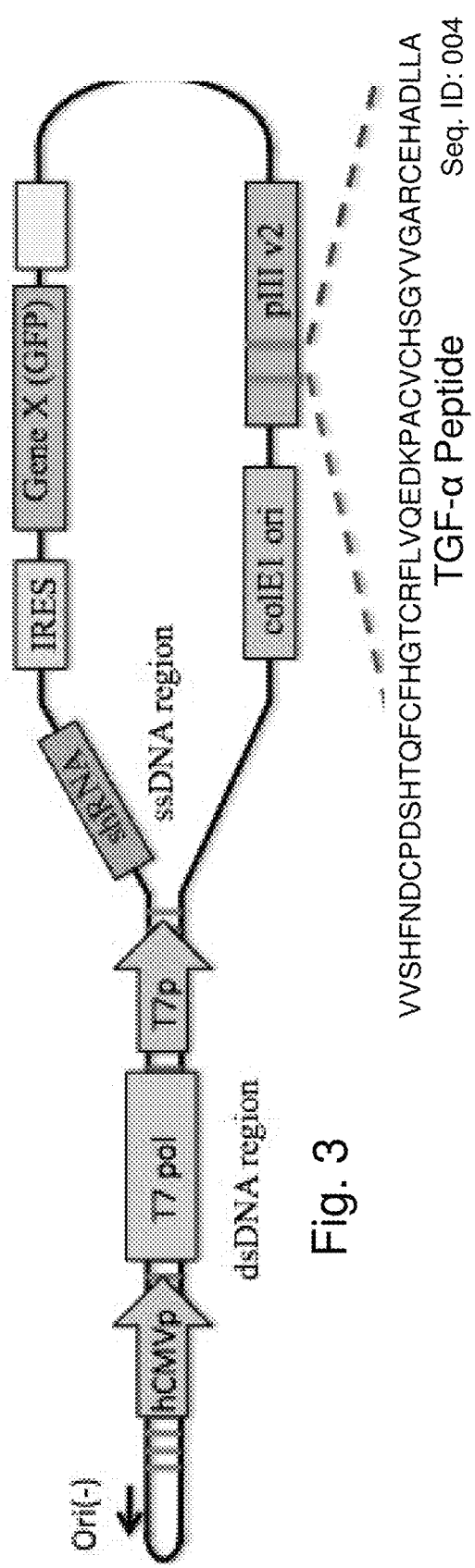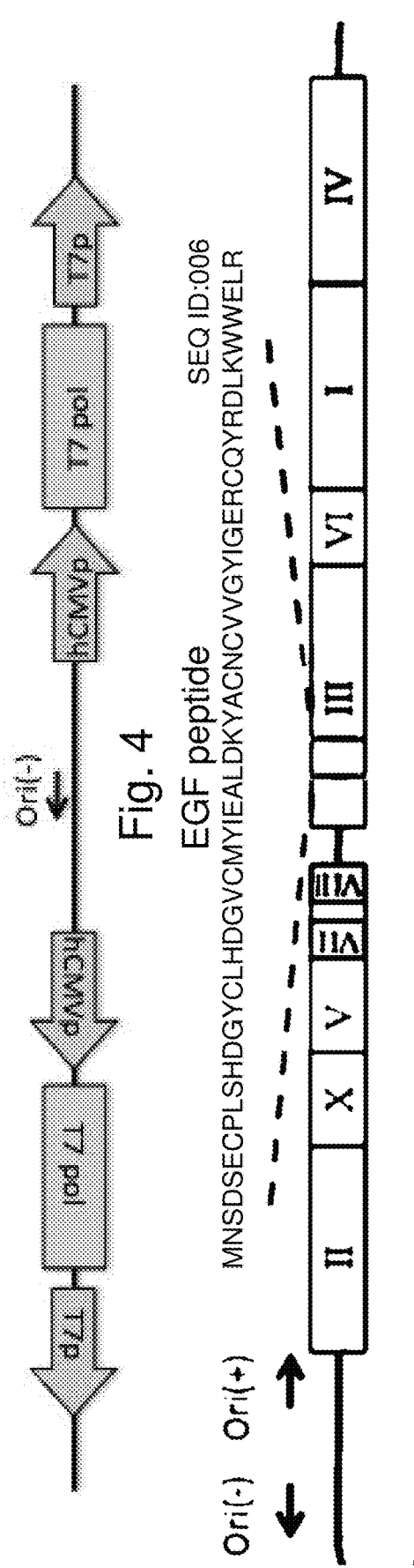

SEQUENCE LISTING

```
<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: Zot domain aa 288-293 of Zonula Oculata toxin

<400> SEQUENCE: 1

Phe Cys Ile Gly Arg Leu
1               5

<210> SEQ ID NO 2
<211> LENGTH: 7
<212> TYPE: PRT
<213> ORGANISM: Artificial Sequence
<220> FEATURE:
<223> OTHER INFORMATION: Submandibular gland peptide T

<400> SEQUENCE: 2

Thr Asp Ile Phe Glu Gly Gly
1               5

<210> SEQ ID NO 3
<211> LENGTH: 10
<212> TYPE: PRT
<213> ORGANISM: Artificial Sequence
<220> FEATURE:
<223> OTHER INFORMATION: Short peptide inhibitory to MMP2 and MMP9

<400> SEQUENCE: 3

Cys Thr Thr His Trp Gly Phe Thr Leu Cys
1               5                   10

<210> SEQ ID NO 4
<211> LENGTH: 50
<212> TYPE: PRT
<213> ORGANISM: Artificial Sequence
<220> FEATURE:
<223> OTHER INFORMATION: TGF-alpha peptide

<400> SEQUENCE: 4

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 5
<211> LENGTH: 47
<212> TYPE: PRT
```

```
<213> ORGANISM: Artificial Sequence
<220> FEATURE:
<223> OTHER INFORMATION: truncated portion of TGF-alpha peptide

<400> SEQUENCE: 5

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
                20                  25                  30

Val Cys His Ser Gly Tyr Val Gly Ala Arg Cys Glu His Ala Asp
            35                  40                  45

<210> SEQ ID NO 6
<211> LENGTH: 54
<212> TYPE: PRT
<213> ORGANISM: Artificial Sequence
<220> FEATURE:
<223> OTHER INFORMATION: EGF peptide

<400> SEQUENCE: 6

Met Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
                20                  25                  30

Asn Cys Val Val Gly Tyr Ile Gly Glu Arg Cys Gln Tyr Arg Asp Leu
            35                  40                  45

Lys Trp Trp Glu Leu Arg
        50

<210> SEQ ID NO 7
<211> LENGTH: 43
<212> TYPE: PRT
<213> ORGANISM: Artificial Sequence
<220> FEATURE:
<223> OTHER INFORMATION: Signal sequence of B5 p6 protein

<400> SEQUENCE: 7

Met Phe Gly Val Lys Arg Ser Trp Leu Arg Arg Trp Val Arg Ala Val
1               5                   10                  15

Ala Ala Phe Ala Val Gly Ala Leu Val Val Gly Val Gly Val Ala
                20                  25                  30

Ser Phe Ala Pro Arg Ala Ser Ala Ala Asn Asp
            35                  40

<210> SEQ ID NO 8
<211> LENGTH: 109
<212> TYPE: RNA
<213> ORGANISM: Artificial Sequence
<220> FEATURE:
<223> OTHER INFORMATION: Anti-miR-203

<400> SEQUENCE: 8
guguugggga cucgcgcgcu gggaccagug guucuuaaca guucaacagu ucuguagcgc    60 aaugugaaa uguuuaggac cacuagaccc ggcgggcgcg gcgacagcg               109

<210> SEQ ID NO 9
<211> LENGTH: 8
<212> TYPE: PRT
<213> ORGANISM: Artificial Sequence
<220> FEATURE:
<223> OTHER INFORMATION: peptide mimic targeting EP3 and EP4

<400> SEQUENCE: 9
```

Glu Gly Val Tyr Val His Pro Val
1               5

<210> SEQ ID NO 10
<211> LENGTH: 49
<212> TYPE: RNA
<213> ORGANISM: Artificial Sequence
<220> FEATURE:
<223> OTHER INFORMATION: siRNA targeting against beta-catenin

<400> SEQUENCE: 10
agcugauauu gauggacagu ucaagagacu guccaucaau aucagcuuu         49

<210> SEQ ID NO 11
<211> LENGTH: 9
<212> TYPE: PRT
<213> ORGANISM: Artificial Sequence
<220> FEATURE:
<223> OTHER INFORMATION: C3a7 analog peptide targeting surface G protein
      coupled receptor

<400> SEQUENCE: 11

Cys Cys Asn Tyr Ile Thr Glu Leu Arg
1               5

<210> SEQ ID NO 12
<211> LENGTH: 8
<212> TYPE: PRT
<213> ORGANISM: Artificial Sequence
<220> FEATURE:
<223> OTHER INFORMATION: C3a9 analog peptide targeting surface G protein
      coupled receptor

<400> SEQUENCE: 12

Asp Cys Cys Asn Tyr Ile Thr Arg
1               5

<210> SEQ ID NO 13
<211> LENGTH: 21
<212> TYPE: DNA
<213> ORGANISM: Artificial Sequence
<220> FEATURE:
<223> OTHER INFORMATION: SiRelA Sense

<400> SEQUENCE: 13
ggugcagaaa gaagacauut t                                       21

<210> SEQ ID NO 14
<211> LENGTH: 21
<212> TYPE: DNA
<213> ORGANISM: Artificial Sequence
<220> FEATURE:
<223> OTHER INFORMATION: SiRelA Antisense

<400> SEQUENCE: 14
aaugucuucu uucugcacct t                                       21

<210> SEQ ID NO 15
<211> LENGTH: 4
<212> TYPE: PRT
<213> ORGANISM: Artificial Sequence
<220> FEATURE:

```
<223> OTHER INFORMATION: Beta-2 integrin binding partner for pro-MMP-9

<400> SEQUENCE: 15

Asp Asp Gly Trp
1
```

US 11,827,890 B1

BACTERIA CARRYING BACTERIOPHAGE AND PROTEASE INHIBITORS FOR THE TREATMENT OF DISORDERS AND METHODS OF TREATMENT

CROSS REFERENCE TO RELATED APPLICATION

The present application is a

Continuation of U.S. patent application Ser. No. 15/456,091, filed Mar. 10, 2017, now U.S. Pat. No. 10,501,746, issued Dec. 10, 2019, which is a Divisional of U.S. patent application Ser. No. 14/180,766, filed Feb. 14, 2014, now U.S. Pat. No. 9,593,339, issued Mar. 14, 2017, which is a Non-Provisional of U.S. Provisional Application No. 61/764,577, filed Feb. 14, 2013, the entirety of which are each expressly incorporated herein by reference.

1. BACKGROUND OF THE INVENTION

1.1. Field of the Invention

This invention is generally in the field of therapeutic delivery systems, including genetically engineered probiotic and attenuated bacteria compositions and methods for providing co-expression of protease inhibitors with plasmids, phage, phagemids and viroids capable of delivering peptides, therapeutic antibodies, DNA and RNA-based therapeutics.

2. BACKGROUND OF THE INVENTION

Citation or identification of any reference herein, or any section of this application shall not be construed as an admission that such reference is available as prior art to the present application. The disclosures of each of the publications cited herein, are hereby incorporated by reference in their entirety in this application, and shall be treated as if the entirety thereof forms a part of this application.

Worldwide, inflammatory and hyperproliferative diseases of the skin, gut, eye, vagina, mouth, nasopharyngeal region and bladder, including cancer, cause substantial morbidity and mortality. Conventional antinflammatory drugs such as corticosteroids offer one of the greatest means of preventing or treating inflammation. Unfortunately, many diseases remain without effective therapies. New therapies, including novel delivery methods and novel therapeutics are needed in order to meet the worldwide challenge of inflammation.

Inflammation is involved in a number of disease pathologies, including acne vulgaris, Alzheimer's, ankylosing spondylitis, arthritis (osteoarthritis, rheumatoid arthritis (RA), asthma, atherosclerosis, atopic dermatitis, atrophic vaginitis, autoimmune diseases, bacterial vaginitis, celiac disease, chronic prostatitis, cancer, colitis, Crohn's disease, dermatitis/eczema, diaper rash, diverticulitis, erythroderma, fibromyalgia, glomerulonephritis, hepatitis, hypersensitivities, inflammatory bowel diseases, interstitial cystitis, irritable bowel syndrome (IBS), lichenoid disorders, lupus erythematous, nephritis, Parkinson's, pelvic inflammatory disease, psoriasis (including flexural, pustular, palmoplantar pustular, nail, acrodermatitis of hallopeau, psoriatic arthritis, and plaque psoriasis), reperfusion injury, rheumatoid arthritis, rosacea, sarcoidosis, sebaceous cysts, systemic lupus erythematous (SLE), transplant rejection, ulcerative colitis vasculitis, or chronic condition known as dystrophic epidermolysis bullosa (DEB), which causes severe blistering and can lead to early deaths from skin cancer.

Parasites and infectious agents are detriments to humans, animals including wild animals, pets and livestock, plants, food and/or the environment (soil, water, etc.) include protozoans, amoebas and helminthes, such as hookworm, intestinal nematodes (roundworms), tissue nematodes including onchocerciasis (river blindness), caused by the nematode *Onchocerca volvulus*, Trichinosis, Dracunculiasis, and the Filariases, Trematodes (Schistosomes and Other Flukes), Cestodes (Tapeworms), Visceral Larva Migrans and other unusual helminth infections, as well as ectoparasitic diseases such as lice (Pediculosis), Scabies, Myiasis and Tungiasis, and mites (including Chigger Syndrome; Mandell, Bennett and Dolin 2010, Principles and Practices of Infectious Diseases, 7th Edition, Elsevier Publishers, 4320 pages). There are five major species of intestinal nematodes found in humans. Because these worms spend a certain amount of time in the soil, they are sometimes known asgeohelminths. The intestinal nematodes include *Ascaris lumbricoides* (the large human roundworm), *Enterobius vermicularis* (the human threadworm or pinworm), *Trichuris trichiura* (human whipworm), human hookworm (*Ancylostoma duodenale* and *Necator americanus*), and *Strongyloides stercoralis* (threadworm).

Treatment of parasitic worms is often difficult. Ivermenctin (22, 23-dihydroavermectin $B_{1a}$+22, 23-dihydroavermectin Bib), marketed under the brand name Mectizan, is currently being used to help eliminate river blindness (onchocerciasis, caused by the nematode *Onchocerca volvulus*) in the Americas and stop transmission of lymphatic filariasis and onchocerciasis around the world. However, the number of effective anti-parasitic therapies is few, and many would-be anti-parasitic compounds are ultimately found to be unsuitable for use in humans and other mammals or birds or wild animals, pets and livestock, because they are not effective at reaching the site of infection.

Bacteria such as *Salmonella, Enterococcus*, and *Escherichia* are known to be able to infect nematodes such as *Caenorhabdus elegans*, but they have not been suggested as anti-parasitic vectors capable of delivering anti-infective phage carrying peptides, antibodies, DNA or RNAs acting as a probiotic within a living host such as a human, nor has the desirability of such a system been recognized. Furthermore, the use of probiotic bacteria such has *Lactococcus, Lactobacillus* or *Bifidobacterium* have not been anticipated or considered desirable in any way for the treatment genetic modulation for the treatment of parasites. To the contrary, bacteria are thought to be used by parasitic nematodes in modulating the immune system to their own advantage (Hayes et al., 2010 Exploitation of the intestinal microflora by the parasitic nematode *Trichuris muris*, Science 328: 1391-1394). New methods to deliver anti-parasitic drugs directly to the site of infection within a host would greatly enhance their effectiveness.

Viruses are among the major infectious diseases worldwide, causing massive worldwide morbidity and mortality from infections including human immunodeficiency virus (HIV), hepatitis virus, influenza virus and many others (Mandell, Bennett and Dolin 2010, Principles and Practices of Infectious Diseases, 7th Edition, Elsevier Publishers, 4320 pages). Virally infected cells may persist for extended periods of time, and new methods for treatment effective at limiting or eliminating viral infection are needed.

Cancer or neoplastic disease including solid tumor, lymphoma, leukemia or leukemic bone marrow, is a devastating condition of uncontrolled cell growth, which often has the ability to spread throughout the body (metastases) resulting in death.

Among the new modalities for a wide range of disease being explored are RNA based therapeutics, including small interfering RNA (siRNA) which results in RNA interference (RNAi) and microRNAs (miRNA). MicroRNAs (miRNA) are single-stranded RNA molecules of, for example, about 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression. In other instances, the therapeutic molecule is an antisense-miRNA, inhibiting the activity of an up-regulated miRNA.

Small interfering RNA (siRNA), sometimes known as short interfering RNA or silencing RNA or RNA interference (RNAi), is a class of 19-25 nucleotide-long double-stranded RNA molecules with 3' overhangs. Asymmetric interfering RNAs have 3' and 5' antisense overhangs and may be only 15 base pairs in length (Sun et al. 2008 Nature Biotechnology 26: 1379-1382, incorporated in its entirety herein). Interfering RNAs play a variety of roles in biology. Most notably, siRNA is involved in the RNA interference (RNAi) pathway, where it interferes with the expression of a specific gene. In addition to their role in the RNAi pathway, siRNAs also act in RNAi-related pathways, e.g., as an antiviral mechanism or in shaping the chromatin structure of a genome.

RNA interference (RNAi) is a powerful means of suppressing the expression of genes, and could potentially be used as a therapeutic intervention to suppress the expression of genes associated with disease. However, delivery of small interfering RNA (siRNA) has generally proven difficult to achieve and new delivery methodologies are eagerly sought. The present invention uses live bacterial vectors as a Trojan horse to deliver ligand modified filamentous phage carrying a siRNA cassette targeted to mammalian cells through the epidermal growth factor receptor (EGFR) and/or other receptors. These phage are packaged within gram-negative bacteria and can be carried to disease-related locations within the body such as the gut where the bacteria occur as normal flora and then be released. Furthermore, highly attenuated gram-negative bacteria such as *Salmonella* have the ability to target solid tumors and therefore have the potential to extend the use of RNAi for the treatment of cancer.

According to Uchida et al., 2011 in regard to the use of siRNA for therapeutic areas such the treatment of the skin (Therapeutic Effects on Atopic Dermatitis by Anti-RelA Short Interfering RNA Combined with Functional Peptides Tat and AT1002 JPET August 2011 vol. 338 no. 2 443-450) ("However, it is not known whether treatment with siRNA is an effective alternative to present medications, such as corticosteroids, and specific questions regarding the skin penetration of siRNA remain unclear. Topical application of naked siRNA does not exert strong therapeutic effects because of its low permeation efficiency owing to various skin barriers and its degradation by enzymes in the body. The most important function of the skin is to form an effective barrier between the internal and external layers of the organism.") Thus, it is apparent that delivery mechanisms that penetrate to the site of the diseased cells or tissues have the potential to overcome present limitations.

The use of live attenuated bacteria as carriers for delivering therapeutics is considered a promising methodology, yet remains without any products approved for clinical use more than years after the concept was first developed (see Kotton and Hohmann 2004, Infection and Immunity 72: 5535-5547 and Roland et al., 2005, Current opinion in Molecular Therapeutics 7: 62-72 for reviews). Among the considerations for achieving therapeutic efficacy by such live attenuated bacteria delivering therapeutics is the form of the therapeutic agent, which may consist of protein, carbohydrate, DNA or RNA-based therapeutics see, e.g., U.S. Pat. Nos. 7,452,531, 7,354,592, 6,962,696, 6,923,972, 6,863,894, 6,685,935, 6,475,482, 6,447,784, 6,190,657, 6,080,849 and US Pub. 2003/0059400, each of which is expressly incorporated herein by reference. Similar hurdles also exist for therapeutic vectors secreting one or more anti-infective proteins or immunomodulatory cytokines such as IL-10 (Steidler and Rottiers, 2006, "Annals of the New York Academy of Sciences 1072:176-186; Neirynck and Steidler 2006, Biotechnology & Genetic Engineering Reviews 22: 253-66; Steidler 2005," Expert opinion on drug delivery 2:737-46).

RNA interference (RNAi) using small interfering RNA (siRNA) or short hairpin RNA (shRNA) molecules is a promising technology for treatment of disease using bacterial delivery technologies (Zhang et al., 2007, Intratumoral delivery and suppression of prostate tumor growth by attenuated *Salmonella enterica* serovar *typhimurium* carrying plasmid-based small interfering RNAs Cancer Research 2007; 67: (12); Manuel et al., 2011, Enhancement of cancer vaccine therapy by systemic delivery of a tumor-targeting *Salmonella*-based STAT3 shRNA suppresses the growth of established melanoma tumors, Cancer Ressearch 71(12) Jun. 15, 2011; Blache et al., 2012, Systemic delivery of *Salmonella typhimurium* transformed with IDS shRNA enhances intratumoral vector colonization and suppresses tumor growth, Cancer Research; 72(24) Dec. 15, 2012). Several authors have suggested the use of bacteria for delivery of RNAi (Andino-Pavlovsky et al U.S. Pat. No. 7,390,646; Andino-Pavlovsky et al. US Patent Application 2005/0118193, Xu et al., WO/2008/091375 Attenuated *Salmonella* as a delivery system for siRNA-based tumor therapy; Li, WO/2009/006450 Bacteria-mediated gene modulation via microRNA machinery; Li, WO/2009/006453 Enabling the use of long dsRNA for gene targeting in mammalian and other selected animal cells; Fruehauf et al., WO/2008/156702 Bacteria mediated gene silencing, Fruehauf et al., WO/2010/057009 *E. coli* mediated gene silencing of beta-catenin; Xu et al., WO/2008/091375 Attenuated *Salmonella* as a delivery system for siRNA-based tumor therapy, Raemaekers, WO/2007/083193 Methods For Controlling Pests Using RNAi, Onyabe and Hone, WO/2010/036391, A Novel RNA-Based Expression System, Gentschev et al., US Patent Application 20110287037 Microorganisms as carriers of nucleotide sequences coding for antigens and protein toxins, process of manufacture and uses thereof), each of which is expressly incorporated herein by reference in its entirety. Others have also suggested the use of siRNA for controlling parasites without using bacteria (Ward and Rhodes, WO2011/017137 Methods and compositions for treating insects and Raemaekers, WO/2007/083193) Methods For Controlling Pests Using RNAi, expressly incorporated herein by reference in its entirety).

Other regulatory RNA molecules are also recognized such as microRNA (miRNA) (Bartel, 2004, MicroRNAs:

Genomics, biogenesis, mechanism and function. Cell 116: 281-297), and it has been proposed that bacteria may also have the ability to deliver miRNA (WO/2009/006450—Bacteria-Mediated Gene Modulation Via Microrna Machinery, expressly incorporated herein by reference in its entirety) and demonstrated by Yoon et al., 2010 Therapeutic effects of recombinant *Salmonella typhimurium* harboring CCL22 miRNA on atopic dermatitis-like skin in mice, Experimental and Molecular Medicine 43: 63-70), expressly incorporated in its entirety by reference herein.

Use of protein toxins for treatment of various disorders including inflammation, autoimmunity, neurological disorders and cancer has long-suffered from off-target toxicity. Some toxins have a natural degree of specificity for their target, such as botulinum toxin which is specific for neurons and is currently marketed as the product known as Botox® (onabotulinumtoxinA). Artificial toxin specificity has been achieved by attachment of a specific antibodies or peptide ligands (e.g., *Pseudomonas* endotoxin A (PE-ToxA) antibody conjugate, known as an immunotoxin). Based upon the binding specificity of the attached antibody moiety for a specific target, enhanced specificity of the target is achieved. Other toxins have been engineered to achieve specificity based upon their sight of activation. For example, aerolysin requires proteolytic activation to become cytotoxic. Substitution of the natural protease cleavage site for a tumor-specific protease cleavage site (e.g., that of the PSA protease or urokinase) results in a toxin selectively activated within tumors. However, in both these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258: 417-424), resulting in a dose-limiting toxicity. Renal injury has occurred in some patients treated with immunotoxins, which may be due to microaggregates of the immunotoxin (Frankel et al., 2001, Blood 98: 722a). Liver damage from immunotoxins is a frequent occurrence that is believed to be multifactorial (Frankel, 2002, Clinical Cancer Research 8: 942-944). To date, antibodies with proteinaceous toxins have limited success clinically. One explanation for the off-target toxicity is that although a specific agent is targeted to the tumor and/or specifically activated there, the agent is also toxic if it diffuses out of the tumor, which is likely to occur due to the high osmotic pressure that occurs within tumors (Jain, R. K., 1994, Barriers to drug delivery in solid tumors, Scientific American 271 (11): 58-65). Once activated inside the tumor and diffused back outside, toxins such as aerolysin remain active and are able to contribute to non-target toxicity.

Protease inhibitors are known as potential drugs for treatment of diseases where proteases play a pivotal role (Turk 2006, Targeting proteases: successes, failures and future prospects. Nature Reviews Drug Discovery 5: 785-799; Motta et al., 2012; Food-grade bacteria expressing elafin protect against inflammation and restore colon homeostasis, Science Translational Medicine 4: 158 158ra144; Vergnolle et al. WO 2011/086172 Recombinant probiotic bacteria for the prevention and treatment of inflammatory bowel disease (IBD) and irritable bowel syndrome (IBS); Edwards et al., (eds) 2008, The Cancer Degradome: Proteases and Cancer Biology, Springer; Rawlings et al., 2010, MEROPS: The Peptidase Database, Nucleic Acids Res. 2010 (Database issue):D227-33, the entirety merops.sanger-.ac.uk/inhibitors/which is expressly incorporated herein by reference; and Bermudes U.S. Pat. No. 8,241,623 B1 Protease sensitivity expression system, each of which is expressly incorporated herein by reference in its entirety.)

There are several protease inhibitors known in bacteria, including ecotin from *E. coli* (Eggers et al., 2004, The periplasmic serine protease inhibitor ecotin protects bacteria against neutrophil elastase, Biochem J. 379: 107-118), the gene product of the inh gene in *Erwinia chrysanthemi* (Letoffe and Wandersman, 1989 Characterization of a protein inhibitor of extracellular proteases produced by *Erwinia chrysanthemi*, Molecular Microbiol 3: 79-86), a protease inhibitor from *Prevotella* (Grenier 1994, Characteristics of a protease inhibitor produced by *Prevotella intermedia* FEMS Microbiol Lett 119: 13-18), *Streptomyces* subtilisin inhibitor (SSI) (Taguchi et al., 1990, Comparison of secretory expression in *Escherichia coli* and *Streptomyces* of *Streptomyces* subtilisin inhibitor (SSI) gene, Biochim Biophys Acta 1049: 278-285) and the *Bacillus* BbrPI (Shiga et al., 1991, Characterization of an extracellular protease inhibitor of *Bacillus brevis* HPD31 and nucleotide sequence of the corresponding gene, Appl. Environ. Microbiol. 58: 525-531). However, their functions remain largely unknown (Kantyka et al., 2010, Prokaryote-derived protein inhibitors of peptidases: A sketchy occurrence and mostly unknown function, Biochimie 92: 1644-1656).

3. OBJECTS OF THE INVENTION

The present invention provides, according to one embodiment, live attenuated bacterial strains that co-express protease inhibitors together with one or more plasmids, phage, phagemids or viroids that carry peptides, antibodies, DNA or RNA based therapeutics. The plasmids phage phagemids or viroids may be carried by either gram negative bacteria, wherein the phage is based on M13, or gram positive bacteria, wherein the phage is based on B5; the viroids which can be carried in either gram positive or gram negative are based on plant viroids or mammalian hepatitis D (Rocheleau L, Pelchat M (2006). "The Subviral RNA Database: a toolbox for viroids, the hepatitis delta virus and satellite RNAs research". BMC Microbiol. 6: 24. doi:10.1186/1471-2180-6-24). The phage are particularly effective in suppressing inflammatory responses through a combination of the effects of the protease inhibitor together with either an externally displayed anti-inflammatory peptide, an externally displayed anti-inflammatory antibody, a DNA encoded anti-inflammatory molecule or a therapeutic RNA, including miRNAs, antisense miRNAs and siRNAs. Certain modifications of the phage, phagemids or viroids may also be useful in treating certain virally infected cells, cancer or parasitic diseases such as worms.

The peptides and antibodies consist of known and/or novel peptides and antibodies that are expressed surface displayed, secreted and/or released by phage, which act either as targeting (receptor:ligand) molecules or directly result in anti-inflammatory, protease-inhibitor, anti-cancer or anti-parasitic or anti-viral activity. The bacterial delivery vector may be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intathecally (intrathecal), by inhaler or nasal spray) or to the mucosal system through oral, nasal, pulmonary intravessically, enema or suppository administration. The terms "oral", "enteral", "enterally", "orally", "non-parenteral", "non-parenterally", and the like, refer to administration of a compound or composition to an individual by a route or mode along the alimentary canal. Examples of "oral" routes of administration include, without limitation, swallowing liquid or solid forms by the mouth, administration of a composition through a nasojejunal or gastrostomy tube, intraduodenal administration of a composition, and rectal administration, e.g., using suppositories that release a live bacterial strain described herein to the lower intestinal tract of the alimentary canal. Upon administration, the bacteria are able to undergo limited or unlimited replication, express, surface display, secrete and/or release the phage and protease inhibitors with anti-inflammatory, anti-cancer, anti-viral or anti-parasitic inhibitory proteins or a combination thereof, and thereby provide a therapeutic benefit by reducing or eliminating the anti-inflammatory, malignancy and/or neoplasia, viral or parasitic disease.

The present invention further encompasses the co-expression by a bacterial expression system, or a combination of bacterial expression systems, of one or more protease inhibitors together with one or more protease sensitive therapeutic agents, which may be the aforementioned phage, or an additional anti-inflammatory, anti-cancer, anti-parasitic or anti-viral agent. The therapeutic agent may be inherently sensitive to proteases, or engineered to have enhanced sensitivity. Within the local high-concentration of the targeted tissue or cells such as the confines of the skin surface, the gut, a solid tumor, lymph node or lumen of a bone, the protease inhibitor prevents the degradation of the therapeutic agent that is therapeutically active against the target tissue such as inflammatory cells, colon cancer cells within a tumor, lymphoma cells within a lymph node, or leukemic cells within the lumen of a bone, virally infected cell or parasitic infection. Upon egress from the confined space of the targeted tissue, the inhibitor falls below the inhibitory concentration, and the therapeutic agent which is protease-sensitive is freely degraded, thus deactivating it outside the target site, resulting in cell or tissue-specific activity as well as increased activity and inactivation in non-target cell or tissues. This surprising solution to the problem of off-target toxicity by a tumor targeting vector stems from the unique localized production of therapeutic agents by bacterial vectors, wherein the active agent is produced locally and subsequently diffuses out, resulting in systemic exposure rather than being injected peripherally with intent to treat distal sites.

When administering self-replicating organisms, the minimum dose approximates a single in vivo replication competent organism or minimum infectious dose, which itself is approximated by an in vitro determined colony forming unit (c.f.u.). However, higher doses are preferred, in order to permit prompt initiation of therapeutic effect and avoid host immune response suppression of the organisms before they reach full therapeutic potential. In some cases, replication incompetent organisms may be used, e.g., where the organisms remain competent to produce virions or other biologically active products as discussed herein, in which case a dose may be, for example, in the range $10^8$ to $10^{10}$ organisms. The maximum dose of preferred organisms which display low toxicity and pathogenicity is in excess of $10^{10}$, and for orally or dermally administered probiotic species, gram scale doses may be administered.

The present invention further encompasses the co-expression by a bacterial expression system, or a combination of bacterial expression systems, of one or more protease inhibitors together with one or more protease sensitive therapeutic agents, which may be the aforementioned phage, or an additional anti-inflammatory, anti-cancer, anti-parasitic or anti-viral agent, whereby the protease inhibitors inhibit antigen processing of endosomal and/or proteosomal proteases, thereby reducing or eliminating immune responses to the bacterial vector and/or the inflammatory disease.

The present invention further encompasses the co-expression by a bacterial expression system, or a combination of bacterial expression systems, of a peptide that modulates tight junctions utilizing the small non-toxic Zonula occuluta toxin (Zot) peptide AT10002 (Song et al. 2008, Enhanced nasal absorption of hydrophilic markers after dosing with AT1002, a tight junction modulator. Eur J Pharm Biopharm 69:231-237) which is the active Zot domain (aa 288-293) with the amino acid sequence: FCIGRL SEQ ID:001.

The present invention encompasses generation of Gram negative bacteria such as *E. coli* and *Salmonella* that are adapted to secrete filamentous phage vectors based on or similar to M13, fd and others that can be directed to infect eukaryotic cells and result in the production delivery of peptide, antibody, DNA or RNA-based therapeutics, such as siRNA molecules that silence eukaryotic gene expression. The phage are produced by attenuated, probiotic or commensal bacteria that are able to reside within the disease site such as the skin, eye, mouth, nasopharynx, gut, vagina, tumor or parasite infected area without themselves causing disease, thus releasing the phage in direct proximity to disease targets. The phage may also contain a novel improvement in their design, by encoding the T7 or phi29 polymerase that recognizes their corresponding strong promoters, T7 and phi29, respectively, that enhance their RNA production efficiency. In addition, the phage may contain a combination or subcombination of other features including 1) a double stranded (inverted repeat) in the promoter region (Prieto and Sanchez, 2007, Self-complementary sequences induce the formation of double-stranded filamentous phages, Biochim Biophys Acta 1770: 1081-1084), 2) a minus (−) strand F' origin of replication which results in greater transcription (Liang, Y. et al., 2006, Better gene expression by (−) gene than by (+) gene in phage gene delivery, Biotechnol. Prog. 22: 626-630), 3) delta-pIII helper phage, which eliminate helper phage background and produce phagemids containing only the pIII targeting ligand (Larocca, et al., 2001, Receptor-targeted gene delivery using multivalent phagemid particles, Molecular Therapy 3: 476-484; Zonghai et al., 2006, Cell-targeted phagemid particles preparation using *Escherichia coli* bearing ligand-pIII encoding helper phage genome, BioTechniques 41: 706-707), 4) an SV40 origin of replication (Larocca et al., 2001), and/or 5) may be used in combination with anti-cancer drugs that enhance phage-based expression (Burg et al., 2002, Enhanced phagemid particle gene transfer in camptothecin-treated carcinoma cells, Cancer Research 62: 977-981). Previously described nucleic acid delivery systems bacteria (Cai, X-M. et al., 2008, Inhibition of cell growth and invasion by epidermal growth factor-targeted phagemid particles carrying siRNA against focal adhesion kinase in the presence of hydroxycamptothecin, BMC Biotechnology 8:74; Jiang, H. et al., 2008, Development of efficient RNA interference system using EGF-displaying phagemid particles, Acta Pharmacol Sin 29: 437-442) have not incorporated these factors, nor have they been delivered inside of a live bacterium. The phage, which express a targeting ligand, or multiple targeting ligands, i.e., are polyvalent, as shown in FIGS. 4 and 5 combined, where the helper phage has one targeting ligand (EGF peptide) inserted into its pIII protein and the phagemid which has a different targeting ligand (TGF-alpha) in its pIII proteins, and thus phage co-produced within the same cell will produce phage with contain both ligands to single or multiple targets, are specific to the disease tissue being treated such as epidermal growth factor receptor (EGFR) which is overexpressed on cancer cells or using other ligands such as an antibody (Rondot, S. et al., 2001, A helper phage to improve single-chain antibody presentation in phage display, Nature Biotechnology 19: 75-78) which adhere to surface receptors on the target cell, can be taken up by the eukaryotic cells that express the receptor and result in a therapeutic effect based on the construction of the phage which could include protein, antibody, DNA or RNA based therapeutics. More than one gene and/or siRNA may be expressed from a single phagemid by employing internal ribosomal reentry signals (IRES s). Commonly used components for eukaryotic expression include a CVM promoter, a polyadenylation signal and SV40 origin of replication. Other polymerases for generating shRNA include the f6 RNA-dependent RNA polymerase (Aalto, A. P. et al., 2007. Large-scale production of dsRNA and siRNA pools for RNA interference using bacteriophage f6 RNA-dependent RNA-polymerase. RNA 13: 1-8). The phage vectors can carry all the necessary elements of the phage genome on a single plasmid/phage/phagemid, or they can be split into two or more plasmids/phage/phagemids (generally known as the helper phage system) or may be localized into the genome or endogenous plasmids.

The present invention also encompasses generation of Gram positive bacteria such as *Lactococcus lactus, Lactococcus casei, Lactobacillus acidophilus, Streptococcus salivarus, Staphylococcus epidermidis* adapted to secrete filamentous phage vectors based on or similar to B5 phage (Chopin et al., 2002 J. Bacteriol. 184: 2030-2033, described further below) that can be directed to infect eukaryotic cells and result in the production delivery of peptide, antibody, DNA or RNA-based therapeutics, such as siRNA molecules that silence eukaryotic gene expression. The phage are produced by attenuated, probiotic or commensal bacteria that are able to reside within the disease site such as the skin, gut, tumor or parasite infected area without themselves causing disease, thus releasing the phage in direct proximity to disease targets. The phage may also contain a novel improvement in their design, by encoding the T7 or phi29 polymerase that recognizes their corresponding strong promoters, T7 and phi29, respectively, that enhance their RNA production efficiency. In addition, the phage may contain a combination or subcombination of other features including 1) a double stranded (inverted repeat) in the promoter region (Prieto and Sanchez, 2007 Self-complementary sequences induce the formation of double-stranded filamentous phages, Biochim Biophys Acta 1770: 1081-1084), 2) a minus (−) strand F' origin of replication which results in greater transcription (Liang, Y. et al., 2006, Better gene expression by (−) gene than by (+) gene in phage gene delivery, Biotechnol. Prog. 22: 626-630), 3) delta-pIII helper phage, which eliminate helper phage background and produce phagemids containing only the pIII targeting ligand (Larocca, et al., 2001, Receptor-targeted gene delivery using multivalent phagemid particles, Molecular Therapy 3: 476-484; Zonghai et al., 2006, Cell-targeted phagemid particles preparation using *Escherichia coli* bearing ligand-pIII encoding helper phage genome, BioTechniques 41: 706-707), 4) an SV40 origin of replication (Larocca, D. et al., 1998, Targeting bacteriophage to mammalian cell surface receptors for gene delivery, Human Gene Therapy 9:2393-2399; Larocca, D. et al., 1999, Gene transfer to mammalian cells using genetically targeted filamentous bacteriophage, FASEB J. 13: 727-734, Larocca, D and Baird, A. 2001, Receptor-mediated gene transfer by phage-display vectors: applications in functional genomics and gene therapy DDT: 793-801; Poul, M.-A. and Marks, J. D. 1999. Targeted gene delivery to mammalian cells by filamentous bacteriophage. J. Mol. Biol. 288: 203-211), and/or 5) may be used in combination with anti-cancer drugs that enhance phage-based expression (Burg et al., 2002, Enhanced phagemid particle gene transfer in camptothecin-treated carcinoma cells, Cancer Research 62: 977-981). Previously described nucleic acid delivery systems bacteria (Cai, X-M. et al., 2008, Inhibition of cell growth and invasion by epidermal growth factor-targeted phagemid particles carrying siRNA against focal adhesion kinase in the presence of hydroxy-camptothecin, BMC Biotechnology 8:74; Jiang, H. et al., 2008, Development of efficient RNA interference system using EGF-displaying phagemid particles, Acta Pharmacol Sin 29: 437-442) have not incorporated these factors nor have they been delivered inside of a live bacterium. The phage, which express a targeting ligand, or multiple targeting ligands to multiple targets (polyvalent), are specific to the disease tissue being treated such as epidermal growth factor receptor (EGFR) which is over expressed on cancer cells or using other ligands such as an antibody (Rondot, S. et al., 2001, A helper phage to improve single-chain antibody presentation in phage display, Nature Biotechnology 19: 75-78) which adhere to surface receptors on the target cell, can be taken up by the eukaryotic cells that express the receptor and result in a therapeutic effect based on the construction of the phage which could include protein, antibody, DNA or RNA based therapeutics. More than one gene and/or siRNA may be expressed from a single phagemid by employing internal ribosomal reentry signals (IRESs). Commonly used components for eukaryotic expression include a CVM promoter, a polyadenylation signal and SV40 origin of replication. Other polymerases for generating shRNA include the f6 RNA-dependent RNA polymerase (Aalto, A. P. et al., 2007. Large-scale production of dsRNA and siRNA pools for RNA interference using bacteriophage f6 RNA-dependent RNA-polymerase. RNA 13: 1-8). The phage vectors can carry all the necessary elements of the phage genome on a single plasmid/phage/phagemid, or they can be split into two or more plasmids/phage/phagemids (generally known as the helper phage system) or may be localized into the genome or endogenous plasmids.

The viroid type vector technology of the present invention is similar to the viroid vectors of Zhou et al., 2011 (Dual functional RNA nanoparticles containing Phi29 motor pRNA and anti-gp120 aptamer for cell-type specific delivery of HIV-1 inhibition, Methods 54: 284-294 with modifications Rocheleau L, Pelchat M (2006). "The Subviral RNA Database: a toolbox for viroids, the hepatitis delta virus and satellite RNAs research". BMC Microbiol. 6: 24. doi: 10.1186/1471-2180-6-24) and the nanoparticles described by Shu et al., 2011 (Assembly of multifunctional phi29 pRNA nanoparticles for specific delivery of siRNA and other therapeutics to target cells Methods: 54: 204-214) adapted as bacterial:eukaryote shuttle vectors delivering therapeutic molecules are modified RNA phage or phagemids that have various combinations or subcombinations of the properties of 1) a eubacterial origin of replication, either gram positive or gram negative, 2) an RNA-dependent RNA-polymerase, such as phi-29, 3) an RNA-based aptamer for cell-targeting, such as targeting a viral entry surface protein (e.g., hemagglutinin for influenza; SU surface protein/TM transmembrane protein for HIV), 4) a eukaryotic viral origin of replication, such as the HIV tRNA primed reverse transcriptase site which generates a single stranded DNA, 5) rolling circle plasmid origin and termination which result in generating a closed double stranded circular DNA, 6) an SV40 origin of replication, and 7) an siRNA specific to the virus, such as an siRNA for HIV Gag/pol or gp120. The viroid may be without any capsid (a true viroid), or contained and secreted within a protease-sensitive capsid (as a novel proviroid) which is then activated by the activity of endogenous proteases at the site generating the viroid wherein co-expressed protease inhibitors do not inhibit the uncoating of the proviroid. An RNase inhibitor, such as the leucine-rich RNasin Ribonuclease Inhibitor® (Promega) may be co-expressed, surface displayed, released or secreted to enhance the stability of the viroid prior to its internalization into the eukaryotic cell.

Anti-Inflammatory Bacteria

The present invention provides, according to one aspect, for example, and without limitation, live bacterial compositions that are genetically engineered to express one or more protease inhibitors combined with plasmids, phagemids, phage or viroids capable of delivering protein, antibody DNA and RNA therapeutics for suppressing inflammatory diseases of the skin, gut, vagina nasopharyngeal region and bladder, including the treatment of cancer.

The present invention also encompasses bacteria suitable for administration to humans and other mammals or birds or wild animals, pets and livestock, that either expressed, released, surface display or secrete proteins including protease inhibitors in combination with plasmids, phage, phagemids or viroids as either expressed, released, surface displayed or secreted by bacteria that are able to deliver peptides, antibodies, DNA or RNA based therapeutics resulting in anti-inflammation as is involved in a number of disease pathologies.

In one embodiment, the bacteria secrete protease inhibitors in combination with anti-inflammatory proteins (Castellani et al., 2007, Anti-chemokine therapy for inflammatory diseases, Int J Immunopathol Pharmacol. 20:447-453; Cianciarullo and Ceccon 2010, Pro-inflammatory and anti-inflammatory cytokines: Homeostasis and/or an imbalance in neonatal sepsis, VDM Publishers, 104 pages: Dinarello 2002, Pro-inflammatory and anti-inflammatory cytokines in rheumatoid arthritis: a primer for clinicians, $3^{rd}$ Edition, Amgen, 351 pages) such as inhibitors of phosphodiesterase 4, IL4, IL-10, IL-1Ra lactoceptin (von Schillde et al., 2012 Lactocepin secreted by *Lactobacillus* exerts anti-inflammatory effects by selectively degrading pro-inflammatory chemokines Cell Host Microbe. 2012 Apr. 19; 11 (4):387-96 22520466) or the tripeptide FEG (Phe-Glu-Gly; FEG) and/or submandibular gland peptide-T (TDIFEGG SEQ ID:002) or adapting the bacteria to secret the *Yersinia* protein LcrV which thereby induces anti-inflammatory IL10. Virally delivered anti-inflammatory proteins adapted to bacterial delivery by addition of a bacterial secretion signal are also encompassed (Zheng et al., virus derived anti-inflammatory proteins: potential therapeutics for cancer, Trends in Molecular Medicine 18: 304-310).

In another embodiment, the bacteria secrete protease inhibitors co-expressed with phage that surface display antibodies against inflammatory agents, such as antibodies against tumor necrosis factor alpha (TNF-alpha) and thereby inhibit TNF-alpha mediated inflammation, or antibodies against TNF-beta, thereby inhibiting TNF-beta mediated inflammation, or antibodies against IL1b thereby inhibiting IL1b mediated inflammation, or antibodies to GM-CSF (e.g., the antigen binding region of the antibody MOR103), thereby inhibiting GM-CSF mediated inflammation, or antibodies against IL12 (e.g., the antigen binding region of the antibody ABT-874), thereby inhibiting IL12 mediated inflammation, or an antibody against IL13 (e.g., the antigen binding region of the antibody CAT354), thereby inhibiting IL13 mediated inflammation, or an antibody against B-lys (e.g., the antigen binding region of lymphostat-BTM), thereby inhibiting B-lys mediated inflammation, or combinations thereof. In another embodiment, the protease inhibitor is coexpressed with phage that delivers one or more miRNA that is anti-inflammatory. In another embodiment, the protease inhibitor is co-expressed with a phage that delivers one or more antisense RNA to an inflammatory associated miRNA, thereby inhibiting that miRNA and reducing inflammation. In another embodiment the protease inhibitor is co-expressed with a phage that delivers one or more siRNA for an inflammatory molecule such as TNF-alpha and/or TNF-beta, thereby reducing or eliminating inflammation.

Expression of antibody deactivating proteins are also encompassed by embodiments of the present invention. The antibody deactivating proteins serve two purposes, one being to prevent the elimination of the bacterial vector, which, while expressing protease inhibitors and various peptides, plasmids, phage, phagemids and/or viroids, may generate an immune response to these heterologous peptides which could results in generating an immune response that would eliminate the bacterial vector. The antibody deactivating protein delays the elimination of the bacteria, resulting in a prolonged delivery of the therapeutic components. Antibody deactivating proteins include the IgA protease from Nisseria (when it is not being used as a fusion protein for secretion or surface display, used primarily in Gram negative bacteria), the IgA protease of *Streptococcus pneumonia* or *Haemophilus*, IdeS (an IgG protease), the IgG protease of *Pseudomonas* (pseudolysin), or *Proteus mirabilis* (mirabilysin), *Treponema* (trepolisin) *Staphylococcus* (glutamyl endopeptidase I GluV8), and EndoS proteases from *Staphalococcus*, the *Staphalococcus* antibody-binding protein A, and Shistosoma IgE proteases. The expression of the antibody deactivating proteins may be under transcriptional control by bacterial promoters that are inducible or constitutive. The antibody deactivating proteins may also contribute to reduced inflammation, since antibodies have the ability to serve as ligands for inflammatory cells such as macrophages, neutrophils, NK cells, dendridic cells and mast cells, their localized reduction by the therapeutic bacteria results in an additional suppression of inflammation. Expression of other immune evasive proteins such as AurA, YopJ and VacA are also encompassed (Coombes, B. K., Valdez, Y., and Finlay, B. B. (2004). Evasive maneuvers by secreted bacterial proteins to avoid innate immune responses. Curr. Biol. 14, R856—R867; Findlay and McFadden 2006, Anti-Immunology: Evasion of the Host Immune System by Bacterial and Viral Pathogens, Cell 124, 767-782), expressly incorporated by reference herein in its entirety.

Expression, or overexpression, of lipoteichoic acid is also encompassed by the embodiments of the present invention. Lipoteichoic acid results in reduced inflammation, is normally produced by gram positive bacteria. Over production by probiotic gram positive bacteria or production in gram negative bacteria (Heaton and Neuhaus 1992, Biosynthesis of D-alanyl-lipoteichoic acid: cloning, nucleotide sequence, and expression of the *Lactobacillus casei* gene for the D-alanine-activating enzyme, J Bacteriol. 174:4707-4717) enhances the anti-inflammatory effect of the bacteria.

Anti-Parasitic and Antiviral Compositions

The present invention comprises bacteria suitable for administration to humans and other mammals or birds or wild animals, pets and livestock, that either expressed, released, surface display or secrete proteins including protease inhibitors in combination with plasmids, phage, phagemids or viroids that are able to deliver peptides, antibodies, DNA or RNA based therapeutics resulting in anti-helminthes, anti-parasitic, or anti-infectious activity. The bacterial delivery vector may be attenuated, non-pathogenic, low pathogenic, or a probiotic bacterium. The bacteria are introduced either systemically (e.g., parenteral, intravenous, intramuscular, intralymphatic, intradermal, subcutaneous), gastrointestinal or the mucosal system through oral, nasal, intravessically or suppository administration where they are able to undergo normal or limited replication, and deliver anti-parasitic inhibitory proteins including protease inhibitors together with plasmids, phage, phagemids or viroids that are able to deliver peptides, antibodies, DNA or RNA based therapeutics targeted against essential parasite proteins, or a combination thereof, and thereby provide a therapeutic benefit to the host by reducing or eliminating the targeted parasite or infectious disease.

The parasites, infectious agents or pests to which the siRNA, shRNA and/or miRNA are targeted are human, animal, livestock, veterinary, food or environmental (soil, water, etc.) organisms including but not limited to hookworm, intestinal nematodes (roundworms), tissue nematodes including *Trichinosis*, Dracunculiasis, and the Filariases, Trematodes (Schistosomes and Other Flukes), Cestodes (Tapeworms), Visceral Larva Migrans and other unusual helminth infections, ectoparasitic diseases, lice (Pediculosis), Scabies, Myiasis and Tungiasis, and mites (including Chigger Syndrome; Mandell, Bennett and Dolin 2010, Principles and Practices of Infectious Diseases, 7$^{th}$ Edition, Elsevier Publishers, 4320 pages). There are five major species of intestinal nematodes found in humans. Because these worms spend a certain amount of time in the soil, they are sometimes known asgeohelminths. The intestinal nematodes include *Ascaris lumbricoides* (the large human roundworm), *Enterobius vermicularis* (the human threadworm or pinworm), *Trichuris trichiura* (human whipworm), human hookworm (*Ancylostoma duodenale* and *Necator americanus*), and *Strongyloides stercoralis* (threadworm). A mouse threadworm, among other animal models, *Syphacia obvelata*, is useful as a model for preliminary testing. Environmental pests include invasive and undesirable species such mud snails and zebra mussels.

The infectious protozoans and amoebas to which the siRNA, shRNA and/or miRNA are targeted are human, animal, food or environmental (soil, water, etc.) protozoans and amoebas, including *Entamoeba histolytica, Giardia lamblia, Balantidium coli, Cryptosporidium parvum* and *Isospora belli* (Mandell, Bennett and Dolin 2009, Principles and Practices of Infectious Diseases, 7$^{th}$ Edition, Elsevier Publishers, 4320 pages) or *Blastocystis* (Poirier et al., 2012, New Insights into *Blastocystis* spp.: A Potential Link with Irritable Bowel Syndrome. PLoS Pathog 8(3): e1002545.)

The infectious viral agents to which the siRNA, shRNA and/or miRNA or antisense miRNA are targeted are viruses, such as HIV, HBV, HCV, influenza (Mandell, Bennett and Dolin 2009, Principles and Practices of Infectious Diseases, 7$^{th}$ Edition, Elsevier Publishers, 4320 pages).

The present invention provides, according to various embodiments, live attenuated, probiotic or commensal bacterial strains such as *Salmonella, E. coli Propionibacterium* or *Lactococcus* or *Lactobacillus* strains that express, release, surface display or secret one or more therapeutic proteins such as a protease inhibitor alone or together with plasmids, phage, phagemids or viroids that are able to deliver peptides, antibodies, DNA or RNA based therapeutics that deliver anti-parasitic toxins or are targeted against essential parasite proteins that are inhibitory, or lethal to parasitic infections such as intestinal worms.

In one embodiment, the live attenuated, probiotic or commensal bacterial strains such as *Salmonella, E. coli* or *Lactococcus* strains express, release, surface display or secret one or more protease inhibitors interfering with the parasite digestive pathway, which is inhibitory, or lethal to parasitic infections such as intestinal worms.

In another embodiment, the live attenuated, probiotic or commensal bacterial strains such as *Salmonella, E. coli, Lactobacillus* or *Lactococcus* strains deliver plasmids, phage, phagemids or viroids that result in siRNA based therapeutics targeted against one or more essential viral genes.

In another embodiment, the live attenuated, probiotic or commensal bacterial strains such as *Salmonella, E. coli* or *Lactococcus* strains deliver plasmids, phage, phagemids or viroids that result in siRNA based therapeutics targeted against one or more essential parasite genes.

In another embodiment, the live attenuated, probiotic or commensal bacterial strains such as *Salmonella, E. coli* or *Lactococcus* strains that express, release, surface display or secret one more protease inhibitors together with one or more anti-parasitic therapeutic proteins whereby the protease inhibitors prevent the degradation of the therapeutic proteins which are inhibitory or lethal to parasitic infections such as intestinal worms.

In another embodiment, the live attenuated, probiotic or commensal bacterial strains such as *Salmonella, E. coli* or *Lactococcus* strains that express, release, surface display or secret one or more therapeutic proteins such as a protease inhibitor together with plasmids, phage, phagemids or viroids deliver DNA based therapeutics targeted against the parasite that express parasite toxic proteins using parasite specific promoters.

In another embodiment, the live attenuated, probiotic or commensal bacterial strains such as *Salmonella, E. coli* or *Lactococcus* strains that express, release, surface display or secret one or more therapeutic proteins such as a protease inhibitor together with plasmids, phage, phagemids or viroids deliver siRNA based therapeutics targeted against one or more essential parasite genes.

In another embodiment, the live attenuated bacterial therapeutic probiotic or commensal bacterial strains such as *Salmonella, E. coli* or *Lactococcus* strains that contain plasmids, phage, phagemids or viroids are inhibitory or lethal to parasitic infections such as intestinal worms are specifically selected for infection and/or hyper-invasiveness into the parasite.

In another embodiment, the live attenuated bacterial therapeutic probiotic or commensal bacterial strains such as *Salmonella, E. coli* or *Lactococcus* strains that contain plasmids, phage, phagemids or viroids are inhibitory or lethal to parasitic infections such as intestinal worms are specifically selected for membrane or cell wall defects that aid in the release of the therapeutic molecules within the target parasite.

These bacterial strains are attenuated or non-pathogenic, safe for administration to reptiles, birds and mammals, including humans or wild animals, pets and livestock, and result in inhibitory or cytotoxic activity against an infectious agent such when administered alone or in combination.

Accordingly, administration to an individual, of a live bacterial vector, in accordance with an aspect of the present invention, that is genetically engineered to express one or more therapeutic proteins with one or more plasmids, phage, phagemids or viroids molecules as described herein has the ability to inhibit or kill infectious agents, resulting in a therapeutic benefit.

A preferred composition will contain, for example, a sufficient amount of live bacteria to produce a therapeutic response in the patient. Accordingly, the attenuated bacterial strains described herein are both safe and useful as live bacterial vectors that can be orally or systemically administered to an individual to provide therapeutic benefit against infectious diseases.

Although not wishing to be bound by any particular mechanism, an example of an effective anti-intestinal anti-parasitic response in humans and other mammals or birds or wild animals, pets and livestock, by administration of genetically engineered, attenuated strains of bacteria as described herein may be due to the ability of such strains to persist in the intestine, infect or be ingested by the parasites to which the therapeutic molecules are specifically targeted, and continuously inhibit those targets, having an anti-parasitic effect. Bacterial strains useful in accordance with a preferred aspect of the invention may carry the ability to produce a therapeutic molecule from an exogenous plasmid, the endogenous virulence plasmid, or chromosomally integrated cassette that encodes and directs expression of one or more therapeutic molecules or be mediated by phage, phagemids or viroids.

The serovars of *Salmonella enterica* that may be used as the attenuated bacterium of the live compositions described in accordance with various embodiments herein include, without limitation, *Salmonella enterica* serovar Typhimurium ("*S. typhimurium*"), *Salmonella montevideo*, *Salmonella enterica* serovar Typhi ("*S. typhi*"), *Salmonella enterica* serovar Paratyphi B ("S. paratyphi 13"), *Salmonella enterica* serovar Paratyphi C ("S. paratyphi C"), *Salmonella enterica* serovar Hadar ("S. hadar"), *Salmonella enterica* serovar Enteriditis ("S. enteriditis"), *Salmonella enterica* serovar Kentucky ("S. kentucky"), *Salmonella enterica* serovar Infantis ("S. infantis"), *Salmonella enterica* serovar Pullorum ("S. pullorum"), *Salmonella enterica* serovar Gallinarum ("S. gallinarum"), *Salmonella enterica* serovar Muenchen ("S. muenchen"), *Salmonella enterica* serovar Anatum ("S. anatum"), *Salmonella enterica* serovar Dublin ("S. dublin"), *Salmonella enterica* serovar Derby ("S. derby"), *Salmonella enterica* serovar Choleraesuis var. kunzendorf ("S. cholerae kunzendorf"), and *Salmonella enterica* serovar minnesota (*S. minnesota*). A preferred serotype for the treatment of bone marrow related diseases is *S. dublin*.

By way of example, live bacteria in accordance with aspects of the invention include known strains of *S. enterica* serovar Typhimurium (*S. typhimurium*) and *S. enterica* serovar Typhi (*S. typhi*) which are further modified as provided by various embodiments of the invention. Such Strains include Ty21a, CMV906, CMV908, CMV906-htr, CMV908-htr, Ty800, aroA-/serC-, holavax, MO1ZH09, VNP20009. See also, U.S. Pat. No. 6,548,287, and EP 0,973,911, each of which expressly incorporated herein by reference. These strains contain defined mutations within specific serotypes of bacteria. The invention also includes the use of these same mutational combinations contained within alternate serotypes or strains in order to avoid immune reactions which may occur in subsequent administrations. In a preferred embodiment, *S. Typhimurium, S. montevideo*, and *S. typhi* which have non-overlapping O-antigen presentation (e.g., *S. typhimurium* is 0-1, 4, 5, 12 and *S. typhi* is Vi, *S. montevideo* is 0-6, 7) may be used. Thus, for example, *S. typhimurium* is a suitable serotype for a first injection and another serotype such as *S. typhi* or *S. montevideo* are used for a second injection and third injections Likewise, the flagellar antigens are also selected for non-overlapping antigenicity between different injections. The flagellar antigen may be H1 or H2 or no flagellar antigen, which, when combined with the three different O-antigen serotypes, provides three completely different antigentic profiles. Methods for deriving heterologous O-antigens have been described by Favre et al., WO/1997/014782, and Roland WO/2000/004919, each of which is expressly incorporated herein by reference.

Novel strains are also encompassed that are, for example, attenuated in virulence by mutations in a variety of metabolic and structural genes. The invention therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., Journal of Bacteriology, 2004) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, pur, purA, purB, purI, purF, zwf, aroA, aroB, aroC, aroD, serC, gua, cadA, rfc, rjb, rfa, ompR, msbB and combinations thereof. Strains of *Salmonella* deleted in stn are particularly preferred.

The invention also encompasses attenuated gram-positive bacteria. For example, *Staphylococcus epidermidis*, group B *Streptococcus* including S. agalaciae, and *Listeria* species including *L. monocytogenes* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033 described further below) may be employed and substituted as needed. Other bacterial strains may also be encompassed, including non-pathogenic bacteria of the gut skin (such as *Staphylococcus epidermidis*, Proprionibacteria) and other body locations known as the human microbiome (Grice et al., Topographical and temporal diversity of the human skin microbiome, Science 324: 1190-1192; A framework for human microbiome research; The Human Microbiome Project Consortium, 14 Jun. 2012 Nature 486, 215-221; Spor et al., 2011, Unravelling the effects of the environment and host genotype on the gut microbiome, Nature Reviews Microbiology 9: 279-290) such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus carnosis*, *Yersinia* sp., *Streptococcus* sp. and *Listeria* sp. Bacteria of low pathogenic potential to humans and other mammals or birds or wild animals, pets and livestock, such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp. (e.g., *Lactobacillus acidophilus, Lactobacillus salivarius*) *Lactococcus* sp., (e.g., *Lactococcus lactus, Lactococcus casei*) *Leuconostoc* sp., *Pediococcus* sp., *Strep-* tococcus sp. (e.g., *S. salivariu, S. thermophilus*), *Bacillus* sp., *Bifidobacterium* sp., *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097; Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878).

It is therefore an object to provide a bacterium co-expressing a protease inhibitor and at least one vector selected from the group consisting of a plasmid, phage, phagemid and a viroid, capable of delivering a therapeutic selected from the group of a peptide, an antibody, DNA and RNA, adapted for treatment of an inflammatory disease in an animal.

The target tissue may be, for example, skin having psoriasis, skin having atopic dermatitis, gut tissue having inflammatory bowel disease, gut tissue with familial adenomatous polyposis, or bladder tissue having in situ bladder cancer.

The vector may comprise, for example, therapeutic RNA is selected from the group consisting of siRNA, miRNA and antisense miRNA, or an anti-TNF-alpha antibody.

It is another object to provide a bacterium co-expressing a protease inhibitor and at least one delivery vehicle selected from the group consisting of a plasmid, a phage, a phagemid and a viroid, capable of delivering a therapeutic selected from the group consisting of at least one of a peptide, an antibody, a DNA-based therapeutic and an RNA-based therapeutic, adapted for treating an infectious disease, the protease inhibitor being expressed in sufficient amount within a localized bacterial colonization region of an animal tissue to inhibit an animal host protease from degrading peptides associated with the therapeutic in the localized bacterial colonization region, but not systemically inhibit the animal host protease outside the localized bacterial colonization region, and the peptide associated with the therapeutic is expressed in a sufficient amount to treat the infectious disease having at least one infectious component proximate to the localized bacterial colonization region.

The infectious disease may be, for example, a parasitic worm. The worm may be selected from the group consisting of *Ascaris lumbricoides, Enterobius vermicularis, Trichuris trichiura, Ancylostoma duodenale, Necator americanus, Strongyloides stercoralis, Trichinosis*, Dracunculiasis, Filariasis, Trematodes, Schistosomes, Flukes, Visceral Larva Migrans, and *Onchocerca volvulus*. The infectious disease may be an intestinal parasite, e.g., an amoeba.

The therapeutic may comprise an RNA-based therapeutic selected from the group consisting of siRNA, miRNA and antisense miRNA.

It is another object to provide a method of treating an animal disease, comprising administering a bacterium to the animal for bacterial colonization of a localized bacterial colonization region, the bacterium co-expressing a protease inhibitor and at least one delivery vehicle selected from the group consisting of a plasmid, a phage, a phagemid and a viroid, which delivers a therapeutic agent selected from the group consisting of at least one of a peptide, an antibody, a DNA-based therapeutic and an RNA-based therapeutic, adapted for treating an animal disease, the protease inhibitor being expressed in sufficient amount by the bacterial colonization of the localized bacterial colonization region to inhibit an animal protease from degrading peptides associated with the therapeutic agent in the localized bacterial colonization region, but not to systemically inhibit the animal protease outside the localized bacterial colonization region, and the peptide associated with the therapeutic is expressed in the localized bacterial colonization region in a sufficient amount to effectively treat the disease.

The disease may be, for example, an inflammatory disease, an infectious disease, or a eukaryotic parasitic disease.

The peptide associated with the therapeutic may comprise a peptide produced by the bacterium. The peptide may be heterologous with respect to the animal. The protease inhibitor may be produced by the bacterium in an inactive form and be activated by the animal.

The peptide associated with the therapeutic may also comprise a peptide produced by animal host cells in response to the therapeutic.

A further object provides a system and method and a genetically engineered organism, which uses co-expression of protease inhibitors and protease sensitive therapeutic agents including phage and phagemids delivering peptides, therapeutic antibodies, DNA and RNA-based therapeutics that results in treating inflammation of a variety of disorders including psoriasis, atopic dermatitis and inflammatory bowel disease. Further provided are bacteria that inhibit the growth of intestinal parasites such as worms, and deliver siRNA or miRNA that have specific anti-parasitic effects that results in the reduction or elimination of the parasite(s).

BRIEF DESCRIPTION OF THE DRAWINGS

FIG. 3 shows a modified ssDNA phage that also contains the T7 polymerase coding sequence and a T7 promoter for shRNA generation.

FIG. 4 shows the linear view of the inverted repeat pCMV and T7 polymerase region that results in dsDNA secondary structure, and depicts polyvalent phage with more than one targeting ligand (EFG and TGF) which are capable of binding one or more receptors.

FIG. 5 shows a helper phage expressing a different targeting peptide in the pIII gene than is expressed in the phage, resulting in multivalent, multi-targeting phage. Together, FIG. 4 and FIG. 5 depict polyvalent phage with more than one targeting ligand (EFG and TGF) which are capable of binding one or more receptors.

6. DETAILED DESCRIPTION OF THE INVENTION

The present invention provides, according to one embodiment, live attenuated bacterial strains that co-express protease inhibitors together with one or more plasmids, phage, phagemids or viroids that carry peptides, antibodies, DNA or RNA based therapeutics. The plasmids, phage, phagemids, or viroids may be carried by either gram negative bacteria, wherein the phage is based on M13, or gram positive bacteria, wherein the phage is based on B5; the viroids which can be carried in either gram positive or gram negative are based on plant viroids or mammalian hepatitis D (Rocheleau L, Pelchat M (2006). "The Subviral RNA Database: a toolbox for viroids, the hepatitis delta virus and satellite RNAs research". BMC Microbiol. 6: 24. doi: 10.1186/1471-2180-6-24). The phage may be particularly effective in suppressing inflammatory responses through a combination of the effects of the protease inhibitor together with either an externally displayed anti-inflammatory peptide, an externally displayed anti-inflammatory antibody, a DNA encoded anti-inflammatory molecule or a therapeutic RNA, including miRNAs, antisense miRNAs and siRNAs. Certain modifications of the phage, phagemids or viroids may also be useful in treating certain virally infected cells, cancer or parasitic diseases such as worms.

The present invention provides, according to various embodiments, improved live attenuated therapeutic bacterial strains that express one or more therapeutic molecules. The primary characteristic of the bacteria of certain embodiments of the invention is the enhanced effect of the effector molecule combination. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more invasion mutations or cell wall defects under the same conditions.

For reasons of clarity, the detailed description is divided into the following subsections: protease inhibitors; phage and targeting ligands, gram negative phage, gram positive phage, viroids, Anti-inflammatory bacteria, identification of essential parasite genes, RNA interference for parasites, and bacteria with invasive ability toward parasitic worms.

6.1 Protease Inhibitors

Figure 1:
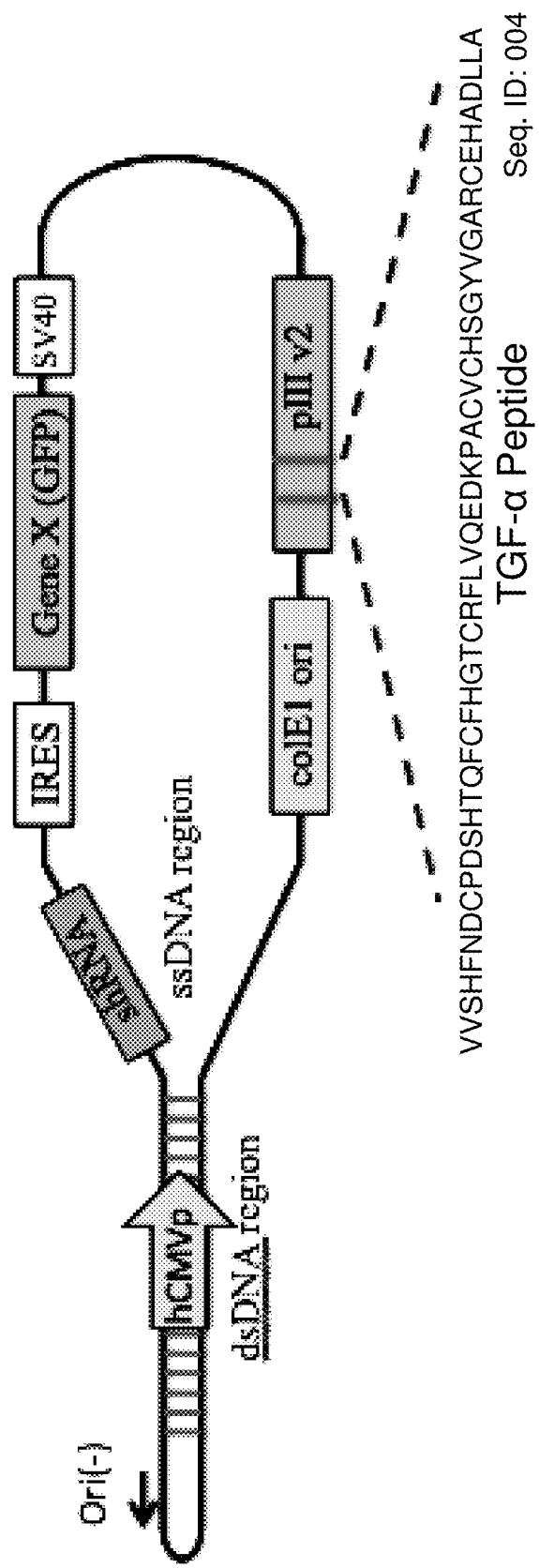
FIG. 1 shows a modified filamentous single stranded (ss) DNA phage, which possesses the human CMV promoter in an inverted repeat, an internal ribosome reentry signal (IRES) and a gene cassette region for expression of auxiliary proteins such as GFP, and the expression portion is terminated with a polyadenylation signal, and an SV40 origin of replication is provided to enhance the copy number of the vector inside the mammalian cell; the pIII gene is modified to display a targeting ligand, and the colEI origin of replication results in a double stranded phagemid when it is carried inside of bacteria, but is packaged as a ssDNA due to the minus (−) strand F' ori.

Protease inhibitors of the invention are preferably based on known polypeptide inhibitors. The inhibitors include both synthetic peptides and naturally occurring, endogenous peptides. To result in the desired activity, the peptides should be surface displayed, released or secreted outside of the bacteria. Accordingly, the peptides are modified by fusing them to secretion signals. The secretion signals may be: N-terminal (LPP:OmpA, M13pIII, M13pVIII, zirS (Finlay et al., 2008, PLoS Pathogens 4 (4), e100003); heat-stable (ST; thermostable) toxins from *Escherichia* and *Vibrio* (U.S. Pat. No. 5,399,490, expressly incorporated herein by reference); *E. coli* enterotoxin II (Kwon et al., U.S. Pat. No. 6,605,697, expressly incorporated herein by reference); by colicin fusions together with colicin lysis proteins, or using autotransporter fusions; fusion to the M13 pIX may also be used (WO 2009/086116, expressly incorporated herein by reference); hlyA C-terminal signal sequence last 60 amino acids of the *E. coli* HlyA hemolysin, together with the required HlyBD supplied in trans and endogenous tolC as shown in FIG. 1.

The N-terminal signal sequences are well known and characterized by the presence of a protease cleavage site for an endogenous bacterial protease. Thus, N-terminal signal sequences provide free protease inhibitors, free from the signal sequence. The C-terminal signal sequence may be further engineered to have a protease cleavage site in between the protease inhibitory peptide and the signal sequence. The cleavage site may be for the same protease that the peptide inactivates. Thus, the protease activates its own inhibitor. The protease cleavage site may also be for a protease other than for the protease inhibitor, thus deactivating another protease. Multiple protease inhibitor peptides may be used in-frame with multiple protease cleavage signals (polymeric protease activated protease inhibitors), where the inhibitors alternate with cleavage sites.

The polymeric protease activated protease inhibitors can be homo- or hetero-inhibitor polymers (i.e., have inhibitors for the same or different proteases, respectively), and/or homo- or hetero-protease cleavage polymers (i.e., have the same or different protease cleavage sites). Proteases upregulated within tumors for which protease cleavage sites may be engineered include: tissue plasminogen activator, activated protein C, factor Xa, granzyme (A, B, M), cathepsin, thrombin, plasmin, urokinase, matrix metaloproteaes, prostate specific antigen (PSA) and kallikrein 2 (e.g., Edwards et al. (eds) 2008, The Cancer Degradome: Proteases and Cancer Biology, Springer, 926 pp), as well as proteases of lysosomes and the gut.

Protease inhibitors have been reviewed by Laskowski and Kato, 1980, (Annual Review of Biochemistry 49: 593-626), expressly incorporated by reference herein. Serine proteases inhibitors, the largest group, include 1) bovine pancreatic trypsin inhibitor (Kunitz) family, 2) pancreatic secretory trypsin inhibitor (Kazal) family, 3) *Streptomyces* subtilisin inhibitor family, 4) soybean trypsin inhibitor (Kunitz) family, 5) soybean proteinase inhibitor (Bowman-Birk) family 6) potato I inhibitor family, 7) potato II inhibitor family, 8) *Ascaris* trypsin inhibitor family, and 9) others. Protease inhibitors have also been grouped within the MEROPS peptidase database (Rawlings et al., 2008 Nucleic Acids Res. 36 Database issue, D320-325). Specific examples of protease inhibitors that may be expressed as complete proteins or peptide fragments corresponding to the active inhibitory site include but are not limited to aprotinin, autodisplay aprotinin (Jose J, Zangen D (2005) Autodisplay of the protease inhibitor aprotinin in *Escherichia coli*. Biochem Biophys Res Commun 333:1218-1226; Jose, 2006, Autodisplay: efficient bacterial surface display of recombinant proteins, Appl Microbiol Biotechnol 69: 607-614), cathepsin inhibitor peptide sc-3130, lympocyte protease inhibitor, maspin, matrix metalloprotease inhibitors, macroglobulins, antithrombin, equistatin, Bowman-Birk inhbitor family, ovomucoid, ovoinhibitor-proteinase inhibitors from avian serum, dog submandibular inhibitors, inter-a-trypsin inhibitors from mammalian serum, chelonianin from turtle egg white, soybean trypsin inhibitor (Kunitz), secretory trypsin inhibitors (Kazal) al proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1 (alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinN11, SerpinN12), cowpea trypsin inhibitor, onion trypsin inhibitor, alpha 1-antitrypsin, *Ascaris* trypsin and pepsin inhibitors, lipocalins, CI inhibiotor, plasminogen-activator inhibitor, collegenase inhibitor, Acp62F from *Drosophila*, bombina trypsin inhibitor, *bombyx* subtilisin inhibitor, von Willebrand factor, leukocyte secretory protease inhibitor. Short peptide inhibitors of protease are preferred. Many protease inhibitors have one or more disulfide bonds. Fusion to thioredoxin (trxA) is known to improve protease inhibitor activity (e.g., Furuki et al., 2007, Fukuoka University Science Reports 37: 37-44). Fusion to glutathione-S transferase (GST) and co-expression with disulfide bond isomerase (DsbA) or nusA (Harrison 2000, Expression of soluble heterologous proteins via fusion with NusA protein. *inNovations* 11: 4-7) are also known to improve solubility. Methods to isolate novel protease inhibitors using M13 phage display have been described by Roberts et al., 1992 (Gene 121: 9-15). Neutrophil serine protease inhibitors derived from elafin (also known as trappin-2 or SKALP (skin-derived anti-leukoproteinase) which targets elastase and proteinase 3) and SLPI (which targets elastase and cathepsin G) have been described as polyvalent inhibitors of neutrophil serine proteases (Zani et al., 2009 Protease inhibitors derived from elafin and SLPI and engineered to have enhanced specificity towards neutrophil serine proteases, Protein Science 2009 18: 579-594). Koivunen et al., (1999 Tumor targeting with a selective gelatinase inhibitor, Nature Biotechnology 17: 768-774) have described a short peptide (CTTHWGFTLC SEQ ID: 003) inhibitory to MMP2 and MMP9 and Bjorklund et al. have described the leukocyte specific β-2 integrin binding partner for pro-MMP-9 "DDGW" (SEQ ID: 015) (Bjorklund et al., 2004 Peptide Inhibition of catalytic and noncatalytic activities of matrix metalloproteinase-9 blocks tumor cell migration and invasion, J. Biol. Chem. 279: 29589-29597). Other peptides include DX-88 which contains the kunitz domain from human lipoprotein-associated coagulation inhibitor domain 1 (LACI-D1) or the variant DX-1000. Calpastatin and novel secreted derivatives including transmembrane transport (i.e., cell penetrating peptides or ferry peptides such as TAT (Heitz et al., 2009, Twenty years of cell-penetrating peptides: from molecular mechanisms to therapeutics Br J Pharmacol. 2009 May; 157(2): 195-206) described herein are also encompassed.

6.2 Phage and Targeting Ligands

Targeting ligands are used to both confer specificity to chimeric proteins or phages, but also to direct internalization (Arap, W., Pasqualini, R. and Ruoslahti, E. 1998. Cancer treatment by targeted drug delivery to tumor vasculature in a mouse model. Science 279: 377-380; Kassner, P. D. et al., 1999, Genetic selection of phage engineered for receptor-mediated gene transfer to mammalian cells. Biochem. Biophys. Res. Com. 264: 921-928; Kay, B. K., Winter, J., McCafferty, J. 1996, Phage Display of Peptides and Proteins, A Laboratory Manual. Academic Press, San Diego; Hoogenboom et al., 1998, Antibody phage display technology and its applications, Immunotechnology 4: 1-20; Pasqualini, R. and Rouslahti, E. 1996. Organ targeting in vivo using phage display peptide libraries. Nature 380: 364-366). The ligands of various aspects of the present invention are peptides that can be expressed as fusions with other bacterially-expressed proteins. The targeting ligands may also be phage displayed single chain antibodies or bispecific antibodies. The targeting ligands may be expressed singly or in multiples of pIII fusions on either the phagemid, helper phage, or both representing the ability to bind more than one target (i.e., are polyvalent, see FIGS. 4 and 5) and result in targeting single or multiple targets where therefore have a lower potential for escape by mutation, since multiple mutations would be required to escape a polyvalent phage that targets multiple receptors.

6.3 Phage/Phagemid Producing Gram-Negative Bacteria Encoding Therapeutic DNA and RNA Molecules.

The F' pilus containing bacterium with deletions relating to conjugation, and expressing a protease inhibitor (PI) that is secreted into the medium, are first infected with a helper phage, such as M13K07 which is able to use the pilus for entry. The helper phage may be further modified to lack an antibiotic resistance marker such as the kanamycin marker. Next, a phagemid (hybrid plasmid:phage which has the F' origin such as one derived from pEFGP-N1) containing a pIII fusion with a targeting peptide, and optionally, a lytic peptide fusion to pVIII, and one or more therapeutic genes which could be a DNA encoding a functional p53 protein, or a gene encoding small interfering RNA molecules (siRNA) or microRNA (miRNA) molecules or other RNA interfering (RNAi) molecules or constructs that mediate RNA interference for an oncogene such as KRAS is transfected into the bacterial cell. The phagemid may also encode the T7 polymerase, and the effector gene such as one encoding the siRNA and/or miRNA and/or RNAi construct may be driven by the T7 promoter. The phage may also contain self-complementary sequences that induce the formation of double-stranded filamentous phage. (Pieto and Sanchez 2007 Biochmica et Biophysica Acta 1770:1081-1084 regarding self-complementary sequences that induce the formation of double-stranded filamentous phage), expressly herein incorporated by reference. Now, the phagemid, in the presence of the helper phage, is replicated as single stranded DNA and packaged into a filamentous phagemid that is secreted outside of the bacterium. Because the phagemid contains pIII fusions with a targeting ligand, such as TGF-alpha, the phage are able to bind to the target cell, enter, and release their DNA, which then is transcribed into the respective therapeutic molecules and results in an antitumor effect. When administered to a patient with a tumor for which the appropriate receptor has been selected, the bacterium carrying the phagemids results in a therapeutic effect. The effect may be further enhanced by co-administration of camptothecin as described by Burg et al. (See, Burg et al., "Enhanced Phagemid Particle Gene Transfer in Camptothecin-treated Carcinoma Cells", Cancer Research 62: 977-981 (2002), expressly incorporated herein by reference.).

6.4 Phage/Phagemid Producing Gram-Positive Bacteria Encoding Therapeutic DNA and RNA Molecules.

The phage are based on B5 (Chopin et al., 2002 J. Bacteriol. 184: 2030-2033). The helper phage may be further modified to lack an antibiotic resistance marker such as the kanamycin marker. Next, a phagemid (hybrid plasmid: phage which has the F' origin such as one derived from pEFGP-N1) containing a pIII fusion with a targeting peptide, and optionally, a lytic peptide fusion to pVIII, and one or more therapeutic genes which could be a DNA encoding a functional p53 protein, or a gene encoding small interfering RNA molecules (siRNA) or microRNA (miRNA) molecules or other RNA interfering (RNAi) molecules or constructs that mediate RNA interference for an oncogene such as KRAS is transfected into the bacterial cell. The phagemid may also encode the T7 polymerase, and the effector gene such as one encoding the siRNA and/or miRNA and/or RNAi construct may be driven by the T7 promoter. The phage may also contain self-complementary sequences that induce the formation of double-stranded filamentous phage. (Pieto and Sanchez 2007 Biochmica et Biophysica Acta 1770:1081-1084 regarding self-complementary sequences that induce the formation of double-stranded filamentous phage, expressly herein incorporated by reference.) Now, the phagemid, in the presence of the helper phage, is replicated as single stranded DNA and packaged into a filamentous phagemid that is secreted outside of the bacterium. Because the phagemid contains pIII fusions with a targeting ligand, such as TGF-alpha, the phage are able to bind to the target cell, enter, and release their DNA, which then is transcribed into the respective therapeutic molecules and results in an antitumor effect. When administered to a patient with a tumor for which the appropriate receptor has been selected, the bacterium carrying the phagemids results in a therapeutic effect. The effect may be further enhanced by co-administration of camptothecin as described by Burg et al. (See, Burg et al., "Enhanced Phagemid Particle Gene Transfer in Camptothecin-treated Carcinoma Cells", Cancer Research 62: 977-981 (2002), expressly incorporated herein by reference.).

6.5 Viroids

The viroid type vectors of the present invention correspond to those of Zhou et al., 2011 (Dual functional RNA nanoparticles containing Phi29 motor pRNA and anti-gp120 aptamer for cell-type specific delivery of HIV-1 inhibition, Methods 54: 284-294 with modifications Rocheleau L, Pelchat M (2006). "The Subviral RNA Database: a toolbox for viroids, the hepatitis delta virus and satellite RNAs research". BMC Microbiol. 6: 24. doi:10.1186/1471-2180-6-24) adapted as bacterial:eukaryote shuttle vectors delivering therapeutic molecules which are modified RNA phage or phagemids that have various combinations or subcombinations of the properties of 1) a eubacterial origin of replication, either gram positive or gram negative, 2) an RNA-dependent RNA-polymerase, such as phi-29, 3) an RNA-based aptamer for cell-targeting, such as targeting a viral entry surface protein (e.g., hemagglutinin for influenza; SU surface protein/TM transmembrane protein for HIV), 4) a eukaryotic viral origin of replication, such as the HIV tRNA primed reverse transcriptase site which generates a single stranded DNA, rolling circle plasmid origin and termination which result in generating a closed double stranded circular DNA, 6) an SV40 origin of replication, and 7) an siRNA specific to the virus, such as an siRNA for HIV Gag/pol or gp120. The viroid may be without any capsid (a true viroid), or contained and secreted within a protease-sensitive capsid (as a novel proviroid) which is then activated by the activity of endogenous proteases at the site generating the viroid wherein co-expressed protease inhibitors do not inhibit the uncoating of the proviroid. An RNase inhibitor, such as the leucine-rich RNasin® Ribonuclease Inhibitor (Promega) may be co-expressed, surface displayed, released or secreted to enhance the stability of the viroid prior to its internalization into the eukaryotic cell.

6.6 Anti-Inflammatory Bacteria

In a preferred embodiment, the probiotic bacteria displays an anti-TNF-alpha antibody or a TNF-beta antibody, either by surface display (Nhan et al., 2011 Surface display of *Salmonella* epitopes in *Escherichia coli* and *Staphylococcus carnosis*, Microbial Cell Factories 2011, 10:22; Lee et al., 2003, Microbial Surface Display, Trends in Biotechnology 21: 45-52; Kramer et al., 2003, Autodisplay: Development of an efficacious system for surface display of antigenic determinants in *Salmonella* vaccine strains, Infec. Immun. 71: 1944-1952) or by carrying a phage that displays the antibody when secreted. The probiotic, commensal or attenuated pathogenic bacterium may be either gram negative, such as *E. coli* or *Salmonella*, or gram positive, such as *lactococcus* or *lactobacillus*. The gram negative bacteria may express and secrete an anti-TNF antibody as a autotransporter display protein or a pIII fusion on a phage such as those derived from M13, fd and other filimentous phage. The Gram positive bacteria will express and secrete an anti-TNF antibody such as an M13 pIII homolog fusion (p6 on a phage such as that derived from B5; Chopin et al. 2005). The antiTNF single chain antibody can be one such as described by Mukai et al., 2006; Yang et al., 2010) and may be fully humanized (United States Patent Application No. 2012/0308575, expressly incorporated herein by reference).

6.7 Co-Expression of Protease Inhibitors with Antiparasitic Bacterial Toxins and Determination of Synergy Proteins with anti-infective activity include bacterial toxins with anti-insect and/or anti-parasite activity include the insecticidal cytotoxins form *Photorhabdus* and *Xenorhabdus* species, anthelmintic cyclic heptapeptide segetalin D (Dahiya 2007, Acta Pol. Pharm. 64: 509-516), cyclodepsipeptids (Dutton et al., J. Med. Chem. 46: 2057-2073) and toxins containing tyrosine and aspartic acid repeats (YD repeats). Proteins with antiparasite activity also include bacterial toxins with anti-insect and/or anti-parasite activity, including those from *Bacillus thuringiensis* (e.g., BT toxin) which have potential for treating parasites and infectious diseases (see Li et al., 2008, Biological Control, 47: 97-102; Li, et al., 2007, Plant Biotechnology Journal 5:455-464; Cappello, M. (2006) Proc. Natl. Acad. Sci. 103(41):15154-15159; Wei J. Z., 2003 Proc. Natl. Acad. Sci. 100:2760-2765, and U.S. Pat. No. 5,281,530, Genes encoding nematode-active toxins cloned from *Bacillus thuringiensis* isolate PS17). Secreted insecticidal toxins and phenol oxidase inhibitors including but not limited to stilbenes from *Photorhabdus* and *Xenorhabdus* species are also encompassed by aspects of the invention. Lectins with anti-parasite activity such those proteins purified from the corms of *Pinellia ternata* and *Lycoris radiata*. Both *P. ternata* agglutinin (PTA) protein and L. *radiata* agglutinin (LRA) as are also encompassed (Gaofu et al., 2008, Journal of Invertebrate Pathology 98: 40-45).

Overall improvement is defined as an increase in effect, such as the ability to inhibit or kill a parasite by the bacteria. The contribution of the enhanced invasion and cell wall defects is determined individually and in combination. Additivity, synergy or antagonism may be determined using the median effect analysis (Chou and Talaly 1981 Eur. J. Biochem. 115: 207-216) or other standard methods.

6.8 Identification of Essential Parasite Genes.

As described by Kemphues K. Essential Genes (Dec. 24, 2005), WormBook, ed. The *C. elegans* Research Community, WormBook, doi/10.1895/wormbook.1.57.1, an essential gene is defined here as a gene necessary for growth to a fertile adult. "In fact, 15-30% of *C. elegans* genes appear to be essential. Approaches for identifying essential genes include several types of classical forward genetic screens, genome-wide RNA interference screens and systematic targeted gene knockout." He continues "There are three types of mutations that identify essential functions: zygotic lethal mutations (lethals), maternal-effect lethal mutations (maternal-effect lethals) and sterile mutations (steriles). Zygotic lethals prevent the development to adult of individuals homozygous for the mutation. Zygotic lethals are broadly categorized, based on the time of developmental arrest, as embryonic or larval lethals. Maternal-effect lethals are a special class of sterilizing mutations that prevent the development of the progeny of hermaphrodites homozygous for the mutation. Such mutations define genes whose expression in the mother is required for embryonic development. Sterile mutations prevent the production of fertilized eggs by individuals homozygous for the mutation. Sterility could arise due to defects in germline development, somatic gonad development, oogenesis, spermatogenesis, ovulation or fertilization. Classically, most lethal and sterile mutations have been identified by random mutagenesis followed by either of two types of screens: genome-wide screens for conditional lethals, such as temperature-sensitive mutations, and screens for non-conditional lethals and steriles in particular genomic regions for which balancers are available. More recently this approach has been augmented and, to a certain extent, replaced by approaches that target individual genes for knockdown or knockout. Two different large-scale screening methods are being used: systematic RNA interference (RNAi) and PCR-based screens for intragenic deletions after mutagenesis. RNAi may be first used to identify the essential gene, and later used as a therapeutic modality."

Essential genes include DNA polymerases, RNA polymerases, tubulins (as described by Kumar et al., 2007, Mining Predicted Essential Genes of *Brugia malayi* for Nematode Drug Targets PLoS ONE 2(11): e1189). Kumar et al. noted that there is good concordance between the phenotypes resulting from the few cases where genes from filarial nematodes have been targeted by RNAi and similar experiments targeting their *C. elegans* orthologs (Aboobaker A A, Blaxter M L (2003) Use of RNA interference to investigate gene function in the human filarial nematode parasite *Brugia malayi*. Mol Biochem Parasitol 129: 41-51; Pfarr K, Heider U, Hoerauf A (2006) RNAi mediated silencing of actin expression in adult Litomosoides sigmodontis is specific, persistent and results in a phenotype. Int J Parasitol 36: 661-669).

6.9 RNA Interference (RNAi) for Parasites.

siRNA for *Caenorhabditis* has been previously analyzed by Maeda et al. (Maeda et al., 2001, Large-scale analysis of gene function in *Caenorhabditis elegans* by high-throughput RNAi, Current Biology 11: 171-176). Identification of homologues of essential *Caenorhabditis* genes is determined using homology searches known to those skilled in the art such as basic local alignment search tool (BLAST). Min et al. (Ming et al., 2010, A modified feeding RNAi method for simultaneous knock-down of more than one gene in *Caenorhabditis elegans*, BioTechniques 48: 229-232) describe methods to affect RNA interference.

6.10 Bacteria with Invasive Ability Toward Parasitic Worms

It has been Known that Certain Bacteria Such as *Salmonella* are Capable of Infecting Certain roundworms, such as Caenorhabdities *elegans* (Lavigne et al., 2008, PLoS ONE 3: e3370; Gereven et al., 2007, FEMS Micobiol Lett 278: 236-241). However, it has not been suggested nor has it been recognized as desirable to construct an attenuated bacterium such as a *Salmonella* that could directly infect roundworms or other parasites following oral ingestion. Nor has it been suggested to engineer any such bacterium to directly attack roundworms or other parasites and to deliver therapeutic RNA molecules that inhibit or kill the parasite.

Bacteria such as *Salmonella, E. coli, lactococcus* are selected for invasiveness towards worms using modified procedures described by Lee et al. (Lee et al., 1992 Identification of a *Salmonella typhimurium* invasion locus by selection for hyperinvasive mutants Proc Natl Acad Sci USA. 1992 89: 1847-1851; Pawelek et al., WO/1996/040238, Vectors For The Diagnosis And Treatment Of Solid Tumors Including Melanoma, expressly incorporated herein by reference), or other methods known to those skilled in the art. The procedure is modified to replace mammalian cells with worm cells or to use whole live worms as targets. The bacteria may also be modified to have foreign DNA from other encoding invasive genes such as the *Yersinia invasin*, *Rickettsia* Sca1, Sca2, Sca3, Sca4, rOmpA, rOmpB (Cardwell and Martinez 2009, Infect. Immun. 77: 5272-5280; Dumler and Walker 2009, Ch. 191—*Rickettsia typhi* (Murine Typhus) in Mandell, Bennett and Dolin 2009, Principles and Practices of Infectious Diseases, 7$^{th}$ Edition, Elsevier Publishers, 4320 pages) and/or escape genes tlyA, tlyC pat1 and pld from *Rickettsia*, whereby the bacteria exhibit enhanced invasion and/or escape from the phagolysosome (Witworth et al., 2005, Infect. Immun. 73: 6668-6673), thereby enhancing the activity of the effector molecules described herein. In a preferred embodiment, the bacteria coexpress pldA, tlyC and Sca2 genes.

7. FIGURE LEGEND

The figures show a circular single-stranded DNA bacteriophage.

FIG. 1 shows a modified filamentous single stranded (ss) DNA phage. The phage possesses the human CMV promoter in an inverted repeat that generates a double stranded (ds) DNA region that enhances gene expression. The pCMV drives the transcription of an shRNA which would be produced in the cytoplasm of the eukaryotic host and bind to the mRNA for the target gene (e.g., b-catenin), marking it for destruction. The vector also contains an internal ribosome reentry signal (IRES) and a gene cassette region for expression of auxiliary proteins such as GFP. The expression portion is terminated with a polyadenylation signal. An SV40 origin of replication enhances the copy number of the vector inside the mammalian cell. The pIII gene is modified to display a targeting ligand such as TGF-a or an EGF peptide that will bind to the EFG receptor (EGFR) on the target cells. The colEI origin of replication results in a double stranded phagemid when it is carried inside of bacteria, but is packaged as a ssDNA due to the minus (−) strand F' ori. FIG. 1 shows inclusion of TGF-α peptide:

SEQ ID: 004
VVSHFNDCPDSHTQFCFHGTCRFLVQEDKPACVCHSGYVGARCEHADLLA

Figure 2:
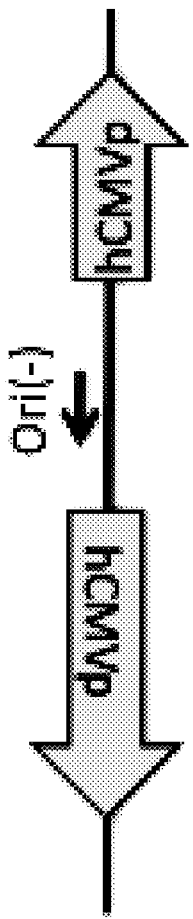
FIG. 2 shows the linear view of the inverted repeat pCMV region that results in dsDNA secondary structure.

FIG. 2 shows the linear view of the inverted repeat pCMV region that results in dsDNA secondary structure.

FIG. 3 shows a modified ssDNA phage that also contains the T7 polymerase coding sequence and a T7 promoter for shRNA generation with a truncated portion of the TGF-α peptide of FIG. 1:

SEQ ID: 005
VVSHENDCPDSHTQFCFHGTCRFLVQEDKPACVCHSGYVGARCEHAD

FIG. 4 shows the linear view of the inverted repeat pCMV and T7 polymerase region that results in dsDNA secondary structure.

FIG. 5 shows a helper phage expressing a different targeting peptide in the pIII gene than is expressed in the phage, resulting in multivalent, multi-targeting phage. FIG. 5 shows an EGF peptide:

SEQ ID: 006
MNSDSECPLSHDGYCLHDGVCMYIEALDKYACNCVVGYIGERCQYRDLKW
WELR

Together FIG. 4 and FIG. 5 depict polyvalent phage with more than one targeting ligand (EFG and TGF) which are capable of binding one or more receptors.

8. EXAMPLES

In order to more fully illustrate the invention, the following examples are provided.

Example 1: Construction of Gram Positive Probiotic Bacteria Expressing Phage which Can be Molecularly Targeted By way of example, the probiotic, commensal or attenuated pathogenic gram positive bacterium may be a *Lactococcus* or *Lactobacillus*. The Gram positive bacteria will express targeting peptides and/or antibodies as a fusion protein with the homologue of the M13 filamentous phage pIII protein, the p6 protein from the filamentous phage B5 (Chopin et al. 2002 Filamentous Phage Active on the Gram-Positive Bacterium *Propionibacterium freudenreichii* J Bacteriol. 184(7): 2030-2033)). The targeting peptides and or antibodies are inserted into the B5 p6 protein immediately after the signal sequence which consists of the 39 amino acids

SEQ ID: 007
MFGVKRSWLRRWVRAVAAFAVGALVVVGVGVASFAPRASAAND the adjacent 40th amino acid A (alanine), followed by synthetically inserted EcoR1, SwaI and BamH1 (which are otherwise absent in the B5 genome, making then unique and useful for addition of targeting sequences) the remainder of the p6 protein using methods known to those skilled in the art. Alternatively, the p6 signal sequence can be replaced with that of usp45 (Loir et al., 2001; Borrero et al., 2011 Use of the usp45 lactococcal secretion signal sequence to drive the secretion and functional expression of enterococcal bacteriocins in *Lactococcus lactis* Applied Microbiology and Biotechnology 89: 131-143; Loir et al., 2001; Signal Peptide and Propeptide Optimization for Heterologous Protein Secretion in *Lactococcus lactis*. Appl Environ Microbiol. 67(9): 4119-4127). The B5 phage genome is further modified to be genetically stable by generating an "addiction" system (Zielenkiewicz and Ceglowski 2001, Mechanisms of plasmid stable maintenance with special focus on plasmid addiction systems, Acta Biochemica *Polonica* 48: 1003-1023) through inserting the *Enterococcus* gene Txe (Grady and Hayes, 2003, Axe-Txe, a broad-spectrum proteic toxin-antitoxin system specified by a multidrug-resistant, Mol Microbiol. 2003 March; 47(5):1419-32) in between the Orf9 and Orf 10 region of B5, and inserting the antitoxin Axe into the host chromosome using methods known to those skilled in the arts. The resulting phage is useful for further modifications as described below for generating probiotic bacteria that express phage with targeting peptides and may deliver protein, DNA or RNA based therapeutics.

Example 2: Construction of Gram Positive Probiotic Bacteria Expressing Phage where the Phage Express an mRNA which can Serve as an RNA Therapeutic The modified B5 phage of Example 1 are further modified using methods known to those skilled in the art to express an mRNA when transfected to a eukaryotic host cell, such as the pCMV promoter which is functional within a eukaryotic host cell together with an adjacent polylinker. The polylinker which in this case carries engineered sites that are otherwise absent in the phage, EcoRV, NdeI, SacI, SspI facilitates cloning of therapeutic DNA and RNA molecules which will generate mRNA transcripts. Addition of an internal ribosomal entry site (IRES) is used to facilitate the targeting of more than one miRNA or deliver of more than one pri-miRNA, or the combination of inhibiting miRNA and delivery of pri-miRNA.

The resulting phage is useful for further modifications as described below for generating probiotic bacteria that express phage with targeting peptides and may deliver protein, DNA or RNA based therapeutics.

Example 3: Single Stranded Anti-miRNA for the Treatment of Psoriasis

The phage used are those described by Bermudes (U.S. Pat. No. 8,241,623, Protease sensitivity expression system, expressly incorporated herein by reference), or as modified further as described in Examples 1 and 2. Anti-miR-203, an miRNA that is upregulated in psoriasis, is targeted using a single-stranded DNA phage generating an RNA transcript with complementary sequence to miR-203:

SEQ ID: 008
GUGUUGGGGACUCGCGCGCUGGGUCCAGUGGUUCUUAACAGUUCAACAGU
UCUGUAGCGCAAUUGUGAAAUGUUUAGGACCACUAGACCCGGCGGGCGCG
GCGACAGCG (Sonkoly, et al., 2007, MicroRNAs: Novel Regulators Involved in the Pathogenesis of Psoriasis? PLoS ONE 2(7): e610. doi:10.1371/journal.pone.0000610). In order to facilitate the phage targeting to karatinocytes, the targeting ligands for fibronectin (Jensen et al. Mol Cell Proteomics. 2003 February; 2(2):61-9 or Zong et al., Keratinocyte growth factor phage model peptides can promote epidermal cell proliferation without tumorigenic effect, Chin Med J (Engl). 2010 May 5; 123(9):1195-2000), or a peptide mimic of KGF (Zong et al., 2009. Screening human keratinocyte growth factor mimic peptide with Ph.D.-7 phage display peptide library. Zhongguo Xiu Fu Chong Jian Wal Ke Za Zhi. 2009 February; 23(2):183-7) is used as a fusion with the phage p6.

A sufficient quantity of the phage containing probiotic bacteria may be applied to the affected area in a liquid or gel to result in suppression of the miRNA target and reduction in the severity or number of psoriasis plaques.

Example 4: Single Stranded Pri-miRNA for the Treatment of Psoriasis

The phage of Example 3 are modified to supply the miR-125b, which is downregulated in psoriasis.

Example 5: siRNA for the Treatment of Psoriasis

Short hairpin RNA (shRNA) are RNA molecules that have self-complementary regions separated by a tight hairpin turn. shRNA can be generated from transcription of a single linear piece of DNA under control of a promoter, a technology that has resulted in the wide-spread use of DNA plasmids for shRNA expression (McIntyre and Fanning 2006. Design and cloning strategies for constructing shRNA expression vectors. BMC Biotechnology 6:1; Myer and Wagner 2006, Recent developments in the application of plasmid DNA-based vectors and small interfering RNA therapeutics for cancer. Human Gene Therapy 17: 1062-1076). shRNA molecules are processed into small interfering RNA (siRNA) that are usually 19-25 nucleotide-long double-stranded RNA molecules with 3' overhangs. Interfering RNAs have the biological effect of targeting mRNA for destruction, thus suppressing gene expression. Treatment of psoriasis uses bacteria with phage that carry keratin 17 siRNA (Chang 2011, Inhibition of keratin 17 expression with antisense and RNAi strategies: exploring novel therapy for psoriasis. Exp Dermatol. 2011 July; 20(7):555-60).

Example 6: Bacteria Expressing miRNA that Inhibits Ulcerative Colitis

The phage used are those described in Example 5 above. The phage target the inhibition of miRNA-21 (Iborra et al., 2012, MicroRNAs in autoimmunity and inflammatory bowel disease: Crucial regulators in immune response Autoimmunity Reviews 11: 305-314). The phage may be further modified to supply pri-miR-193 and inhibit miR375.

Example 7: Bacteria Expressing miRNA that Inhibits Bladder Cancer

The bacteria and phage used are those described Examples 1 and 2. The phage are targeted to the cancer cells by the EFG or TGF peptides (Wallerand et al., 2010, Phospho-Akt pathway activation and inhibition depends on N-cadherin or phospho-EGFR expression in invasive human bladder cancer cell lines, Urolgic Oncology: Seminars and Original Investigations 28: 180-188). The phage mRNA transcript(s) target the inhibition of hsa-miR-183, hsa-miR-200b~429, hsa-miR-200c~141 and hsa-miR-17~92 clusters (Han et al., MicroRNA Expression Signatures of Bladder Cancer Revealed by Deep Sequencing PLoS ONE 6(3): e18286. doi:10.1371/journal.pone.0018286) which were are significantly upregulated.

Example 8: Bacteria Expressing siRNA that Inhibits Bladder Cancer

The bacteria and phage used are those described Examples 1 and 2. The phage are targeted to the cancer cells by the EFG or TGF peptides (Wallerand et al., 2010, Phospho-Akt pathway activation and inhibition depends on N-cadherin or phospho-EGFR expression in invasive human bladder cancer cell lines, Urolgic Oncology: Seminars and Original Investigations 28: 180-188). The phage mRNA transcript(s) target the inhibition of survivin by delivering an siRNA (Ning et al., 2004. siRNA-mediated down-regulation of survivin inhibits bladder cancer cell growth Int J Oncol. 2004 October; 25(4):1065-71). The bacteria may be further engineered to secrete an anticancer cytotoxin, such as nisin (Joo et al., 2012 Nisin, an apoptogenic bacteriocin and food preservative, attenuates HNSCC tumorigenesis via CHAC1, Cancer Medicine 2012; 1(3): 295-305) or those described by Bermudes (U.S. Pat. No. 8,241,623, expressly incorporated herein by reference). An effective amount of the bacteria may be administered intrathecally.

Example 9: Bacteria Expressing siRNA that Inhibits Familial Adenomatous Polyposis The bacteria and phage used are those described Examples 1 and 2. The phage are targeted to the enterocytes by mucosal prostanoid receptors such as EP3 and EP4 present in familial adenomatous polyposis (Takafugi et al., 2001, Mucosal prostanoid receptors and synthesis in familial adenomatous polyposis. Histochem Cell Biol. 2001 August; 116(2):171-81) using a peptide such as the peptide mimic:

H₂N-Glu-Gly-Val-Tyr-Val-His-Pro-Val-COOH
SEQ ID:009 engineered into the gram (−) phage pIII protein or the gram (+) phage p6 protein for phage surface display. (Budisavljevic et al., 1992, Antagonist effect of a receptor-mimicking peptide encoded by human angiotensin II complementary RNA. Hypertension April; 19(4):345-54.). The siRNA is targeted against beta-catenin using a sequence:

SEQ ID: 010
AGCUGAUAUUGAUGGACAGUUCAAGAGACUGUCCAUCAAUAUCAGCUUU previously described (Xiang et al., 2006, Short hairpin RNA—expressing bacteria elicit RNA interference in mammals Nature Biotechnology 24, 697-702). An effective amount of the bacteria are administered orally.

Example 10: Bacteria Expressing miRNA that Inhibits Familial Adenomatous Polyposis The bacteria and phage used are those described Examples 1 and 2.

Example 11: Bacteria Expressing miRNA that Inhibits Atopic Dermatitis (AD, a Type of Eczema)

The bacteria and phage used are those described Examples 1 and 2. The phage are targeted to the surface G protein coupled receptor (GPCR) C3aR of mast cells through the synthetic C3a analogue peptides (CCNYITELR SEQ ID:011) designated C3a7 and C3a9 (DCCNYITR SEQ ID:012) (Peterfy et al., 2008 C3a-derived peptide binds to the type I FccR and inhibits proximal-coupling signal processes and cytokine secretion by mast cells. International Immunology 20: 1239-1245; and WO/2009/0075898 Israel Pecht, Anna Erdei, Complement C3A Derived Peptides and Uses Thereof) as fusions engineered into the gram (−) phage pIII protein or the gram (+) phage p6 protein for phage surface display, expressly incorporated herein by reference. The phage are designed to inhibit MiR-155, which is over expressed (Sonkoly et al., 2010. MiR-155 is overexpressed in patients with atopic dermatitis and modulates T-cell proliferative responses by targeting cytotoxic T lymphocyte—associated antigen 4, J Allergy Clin Immunol. 2010 September; 126(3):581-9.e1-20). An effective amount of the bacteria are administered topically.

Example 12: Bacteria Expressing siRNA that Inhibits Atopic Dermatitis (AD, a Type of Eczema)

The bacteria and phage used are those described Examples 1 and 2. The phage are targeted to the surface G protein coupled receptor (GPCR) C3aR of mast cells through the synthetic C3a analogue peptides (CCNYITELR SEQ ID:011) designated C3a7 and C3a9 (DCCNYITR SEQ ID:012) (Peterfy et al., 2008 C3a-derived peptide binds to the type I FccR and inhibits proximal-coupling signal processes and cytokine secretion by mast cells. International Immunology 20: 1239-1245; and WO20090075898 Israel Pecht, Anna Erdei Complement C3A Derived Peptides and Uses Thereof, expressly incorporated herein by reference). The phage are designed to inhibit RelA using short interfering RNA siRNA (Uchida et al., 2011. Therapeutic Effects on Atopic Dermatitis by Anti-RelA Short Interfering RNA Combined with Functional Peptides Tat and AT1002 JPET August 2011 vol. 338 no. 2 443-450) with the sequences SiRelA Sense

```
                                        SEQ ID 013
    5' GGU GCA GAA AGA AGA CAU UdTdT 3'
``` and Antisense

```
                                        SEQ ID 014
    5' AAU GUC UUC UUU CUG CAC CdTdT 3'si.
```

Example 13: Bacteria Expressing Phage that Deliver Functional Antibodies Against TNF-Alpha The bacteria and phage used are those described Examples 1 and 2. The phage are targeted to tumor necrosis factor alpha, an inflammatory cytokine present in inflammatory diseases such as inflammatory bowel disease, by engineering them to express anti-TNF-alpha antibodies as a fusion with the pIII protein. The phage are constructed as single chain antibodies (Mukai et al., 2006 Optimization of anti-tumor necrosis factor-alpha single chain Fv displayed on phages for creation of functional antibodies. Pharmazie 61: 889-890; Yang et al., 2010 Construction and Characterization of Single Chain Fv Phage display Library Against tumor necrosis factor alpha. Chinese Journal of Biochemistry and Molecular Biology 26: 930-936) and the antibody may be further "humanized" (Full Human Anti-TNF-Alpha Monoclonal Antibody, Preparation Method And Use Thereof United States Patent Application 2012/0308575, expressly incorporated herein by reference). The bacteria may then be administered to a patient with an inflammatory disease, for example orally administered to a patient with inflammatory bowel disease, whereby the bacteria then proliferate within the gut, and in such locations that TNF-alpha mediates inflammation, the antibody binds to the TNF-alpha, thereby neutralizing its inflammatory effect and diminishing or eliminating the inflammatory symptoms.

Example 14: Bacteria Expressing Phage that Deliver Functional Bispecific Antibodies The bacteria and phage used are those described Examples 1 and 2. The phage are targeted to cancerous targets that induce apoptosis (Kontermann, 2005. Recombinant bispecific antibodies for cancer therapy Acta Pharmacologica *Sinica* 26, 1-9; Hermann et al., 2008, Construction of Optimized Bispecific Antibodies for Selective Activation of the Death Receptor CD95 doi: 10.1158/0008-5472.CAN-07-6175 Cancer Res 68; 1221; Chang 2005, Bispecific antibodies for inducing apoptosis of tumor and diseased cells WO/2005/014618A2, expressly incorporated herein by reference).

The phage used are those described by Bermudes (U.S. Pat. No. 8,241,623, Protease sensitivity expression, expressly incorporated herein by reference in its entirety). The chimera consists of the M13 filimentous phage pIII protein 18 amino acid signal sequence, followed by the natural alanine and a 3 glycine.

The bacteria may also simultaneously express an anti-inflammatory cytokine, such as IL10 (Steidler et al., U.S. Pat. No. 6,746,671, expressly incorporated herein by reference in its entirety) and a protease inhibitor, such as trappin (elafin; Food-grade bacteria expressing elafin protect against inflammation and restore colon homeostasis, Science Translational Medicine 4: 158 158ra144).

Example 15: Identification of Microbiome Bacteria Secreting Protease Inhibitors Secreted protease inhibitors of the human microbiome are determined from individual bacteria or mixed colonies of bacteria collected from human body sites by culturing the bacteria and screening for zones of protease inhibition. First, the cognate protein, e.g., collagen, or collagen fragments (gelatin), is embedded into a nutrient agar using methods known to those skilled in the arts. Second, a proteolytic bacterium of the human microbiome is grown under conditions for which it produces an exoenzyme protease, such as that for collagen or gelatin, the secretion of such which can be determined using the said gelatin-containing agar plate (Vermelho et al., 1996, Detection of Extracellular Proteases from Microorganisms on Agar Plates Mem Inst Oswaldo Cruz, Rio de Janeiro, Vol. 91(6): 755-760). Non-proteolytic bacteria are incubated on the gelatin agar plate, which may be a mixed culture including known or unknown organisms, and then replica plated to generate a master plate, to later recover bacteria of interest. The gelatin plate is then flooded with the exoenzyme protease supernatant and incubated for a sufficient time to degrade all of the gelatin embedded within the plate. The protease plate is then "developed" by precipitating undigested protein using 15% trichloroacetic acid (TCA). For microbiome bacteria secreting protease inhibitors, a halo of precipitated, undigested protein is observed due the presence of a protease inhibitor, and the corresponding bacterium selected from the master plate.

Example 16: Identification of Novel Secreted Protease Inhibitors

The secreted protease inhibitors as derived in the Example identified above are inherently capable of secreting a protease inhibitor into the media. Supernatants of the media containing the protease are collected by centrifuging the bacteria and passing the supernatant through a 0.22 µm filter. Then, in a novel modification of protease zymography (Lantz and Ciborowski 1994, Zymographic techniques for detection and characterization of microbial proteases. Methods Enzymol. 1994; 235:563-594), a native, non-denaturing gel containing the cognate protein gelatin is run in duplicate, one with embedded gelatin and one without embedded gelatin. Rather than running a protease in the gel, the protease inhibitor supernatant is run. For the gelatin-embedded gel, the gel is then incubated in the exoenzyme protease supernatant which then digests all of the gelatin protein, except at the location of the protein band of the peptide protease inhibitor, which is determined by developing in 15% TCA (Hanspal et al., 1983, Detection of protease inhibitors using substrate-containing sodium dodecyl sulfate-polyacrylamide gel electrophoresis, Anal Biochem. 132 (2): 288-293). The duplicate gel is stained, the appropriate corresponding gel band is excised from the gel. The protein is identified using MALD-TOF.

Example 17: Identification of a Novel Secreted Inhibitor of ICE

Group A *Streptococcus, S. pyogenes*, secrete a protease (streptococcal pyrogenic exotoxin B) speB that functions as an interleukin 1 converting enzyme (ICE), a protease that activates interleukin 1 beta precursor into the active pro-inflammatory cytokine (Lukomski et al., 1998, Genetic Inactivation of an Extracellular Cysteine Protease (SpeB) Expressed by *Streptococcus pyogenes* Decreases Resistance to Phagocytosis and Dissemination to Organs Infect Immun. 1998 February; 66(2): 771-776). SpeB also activates a human matrix metalloprotease (Burns et al., 1996. Activation of a 66-kilodalton human endothelial cell matrix metalloprotease by *Streptococcus pyogenes* extracellular cysteine protease. Infect Immun. 64:4744-4750) which may further contribute to pathogenesis. IL1 contributes to the inflammation associated with psoriasis. Detection of bacteria, including human microbiome bacteria of the skin and other locations that are capable of producing inhibitors of speB are detected using a the fluorescent protein assay for speB described by Kansal et al. (Kansal et al., 2000, Inverse Relation between Disease Severity and Expression of the Streptococcal Cysteine Protease, SpeB, among Clonal MITI Isolates Recovered from Invasive Group A Streptococcal Infection Cases, Infect Immun. 2000 November; 68(11): 6362-6369) except that the fluorescent substrate is incorporated into a nutrient agar plate. The speB protein is purified as described by Kansal et al., 2000, and the protease inhibitor assay for microbiome bacteria as described in Example 15 is performed, except that the plate is viewed with ultraviolet light through a filter that passes red fluorescence. The inhibitor is then purified and identified as described in Example 16.

Example 18. Use of Microbiome Bacteria for the Treatment of Psoriasis and Other Inflammatory Skin Diseases The purified protease inhibitor bacteria of Example 17 is used for treatment of psoriasis. A sufficient amount of the bacteria are applied to the affected sites in a saline formulation to result in colonization and inhibition of the inflammatory response, resulting in decrease in the size and/or number of inflammatory lesions.

Example 19. Use of Protease Inhibitor for the Treatment of Psoriasis

The purified protease inhibitor protein of Example 17 is used for treatment of psoriasis. A sufficient amount of the substantially purified protease inhibitor, obtained using standard protein purification procedures known to those skilled in the art, is applied to the affected sites in a saline or gel formulation to result in inhibition of the inflammatory response, resulting in decrease in the size and/or number of inflammatory lesions.

Example 20. Use of Probiotic Bacteria for the Treatment of Psoriasis and Other Inflammatory Skin Diseases Other purified protease inhibitors may be expressed within probiotic bacteria for treatment of psoriasis. Other proteases include elafin as expressed by a *lactococcus* or *lactobacillus* using methods known to those skilled in the art. A sufficient amount of the bacteria are applied to the affected sites in a saline formulation to result in colonization and inhibition of the inflammatory response, resulting in decrease in the size and/or number of inflammatory lesions.

Example 21. Treatment of Inflammatory Bowel Disease

A treatment is provided for inhibiting production of pro-inflammatory cytokines (including TNF-α and IL-1β) and promoting production of anti-inflammatory cytokines (including IL-10). Probiotic bacteria can be constructed in *Lactobacillus* using methods known to those skilled in the art which simultaneously express and secrete IL-10, an IL-10 protective protease inhibitor such as aprotinin, and an ICE inhibitor as described in Example 17.

The phage used are those described by Bermudes (U.S. Pat. No. 8,241,623, Protease sensitivity expression, expressly incorporated herein by reference). The chimera consists of the M13 filimentous phage pIII protein 18 amino acid signal sequence, followed by the natural alanine and a 3 glycine spacer. The spacer is followed by the mature 50 amino acid peptide for KGF-peptide, the remaining pIII protein.

The entire chimeric effector protein and expression cassette components are synthesized using standard DNA synthesis techniques, for example, at a contract DNA synthesis facility, and cloned into a chromosomal localization vector, e.g., an IS200 deletion vector, and integrated into the chromosome (Donnenberg and Kaper, 1991, Low et al., 2003, each of which is expressly incorporated herein by reference).

Example 22: Construction of RNA Molecules

RNA molecules are constructed using methods known to those skilled in the art (such as described in siRNA Design Guidelines, Technical Bulletin #506, Applied Biosystems; Naito et al., 2004, SiDirect: Highly effective, target-specific siRNA design software, Nucleic Acids Research 43: W124-W129).

Example 23: Therapeutic Efficacy Against Parasites

Therapeutic efficacy is achieved by a modification of Min et al. (Min et al. 2010, A modified feeding RNAi method for simultaneous knock-down of more than one gene in *Caenorhabditis elegans*, BioTechniques 48: 229-232), wherein the "feeding" is the introduction of live bacteria into a host, such as through injection of a capsule containing live bacteria. The host is monitored for the presence and number of the target parasite.

The method of the invention for inhibiting growth or reducing the number of worms or other parasites comprises administering to a patient having, or prior to having, a worm or other parasite, an effective amount of an isolated mutant *Salmonella* sp. or other attenuated, commensal or probiotic bacteria comprising the ability to deliver a therapeutic RNA to a sensitive worm or parasite, said mutant being capable of attaching to, internalizing or residing within proximity to the worm or parasite when administered in vivo. Sensitivity is defined as the effective concentration at which the worm or parasite proliferation is affected, or the concentration at which the viability of the worm or parasite, as determined by recoverable units, is reduced.

When administered to a patient, e. g., an animal for veterinary use or to a human for clinical use, the mutant bacteria can be used alone or may be combined with any physiological carrier such as water, an aqueous solution, normal saline, or other physiologically acceptable excipient.

In general, the dosage ranges from about 1.0 cfu/kg to about $1 \times 10^{10}$ cfu/kg; optionally from about 1.0 cfu/kg to about 1×10⁸ cfu/kg; optionally from about 1×10² cfu/kg to about 1×10⁸ cfu/kg; optionally from about 1×10⁴ cfu/kg to about 1×10⁸ cfu/kg.

The mutant bacteria of the present invention can be administered by a number of routes, including but not limited to: orally, suppository, topically, injection including, but not limited to, intravenously, intraperitoneally, subcutaneously, intramuscularly, intratumorally, i.e., direct injection into the site of infection, etc.

It will be understood that the foregoing is only illustrative of the principles of the invention, and that various modifications can be made by those skilled in the art without departing from the scope and spirit of the invention.

What is claimed is:

1. A genetically engineered bacterium, comprising:
a first genetic construct adapted to express a heterologous protease inhibitor for secretion from the bacterium in a sufficient amount to inhibit an environmental protease, and
a second genetic construct adapted to express a delivery vehicle for secretion from the bacterium, comprising a plurality of different peptides, selected from the group consisting of a plasmid, a phage, a phagemid and a viroid, adapted to deliver a therapeutic agent for treating a disease, selected from the group consisting of at least one of a peptide, a DNA-based therapeutic and an RNA-based therapeutic,
wherein the therapeutic agent is adapted for treating an inflammatory disease.

2. The genetically engineered bacterium according to claim 1, wherein the therapeutic agent comprises a peptide having a high affinity binding characteristic for a predetermined ligand.

3. The genetically engineered bacterium according to claim 1, wherein the therapeutic agent comprises a DNA-based therapeutic.

4. The genetically engineered bacterium according to claim 1, wherein the therapeutic agent comprises an RNA-based therapeutic.

5. The genetically engineered bacterium according to claim 1, wherein the protease inhibitor is present in a sufficient amount to increase an efficacy of the at least one therapeutic agent for treatment of a human disease by administration of the genetically engineered bacterium to the human.

6. The genetically engineered bacterium according to claim 1, wherein the at least one therapeutic agent is directly toxic to a eukaryotic animal parasite.

7. The genetically engineered bacterium according to claim 1, wherein at least one therapeutic agent comprises a genetically engineered chimeric toxin.

8. The genetically engineered bacterium according to claim 1, wherein the genetically engineered bacterium is adapted to colonize an animal host, and the heterologous protease inhibitor is produced by the bacteria in an inactive form and is activated by the animal host.

9. The genetically engineered bacterium according to claim 1, wherein the therapeutic agent comprises an externally displayed anti-inflammatory peptide.

10. The genetically engineered bacterium according to claim 1, wherein the therapeutic agent comprises a DNA-based therapeutic that encodes anti-inflammatory molecule.

11. The genetically engineered bacterium according to claim 1, wherein the therapeutic agent comprises a DNA-based therapeutic that encodes a therapeutic RNA.

12. The genetically engineered bacterium according to claim 1, wherein the therapeutic agent comprises a peptide or encodes a peptide, having a protease cleavage site for a respective protease, and the protease inhibitor is configured to inhibit the respective protease.

13. The genetically engineered bacterium according to claim 1, wherein the protease inhibitor is fused to a secretion signal.

14. The genetically engineered bacterium according to claim 13, wherein the protease inhibitor is fused to the secretion signal through an intervening protease cleavage site for an endogenous bacterial protease.

15. The genetically engineered bacterium according to claim 1, wherein the protease inhibitor is provided as part of a polymer of a plurality of protease inhibitors and a plurality of intervening protease cleavage sites.

16. The genetically engineered bacterium according to claim 1, wherein both the protease inhibitor and the therapeutic agent are each heterologous to the genetically engineered bacterium.

17. The genetically engineered bacterium according to claim 1, wherein the delivery vehicle is adapted to be activated by a respective protease to make the therapeutic agent available, and the protease inhibitor does not inhibit the respective protease to prevent activation of the delivery vehicle.

18. The genetically engineered bacterium according to claim 1, wherein the therapeutic agent comprises a bacterial toxin with at least one of anti-insect and anti-parasite activity.

19. A genetically engineered bacterium, comprising:
a first genetic construct encoding a secretable heterologous protease inhibitor,
a second genetic construct encoding a secretable delivery vehicle, the secretable delivery vehicle comprising a peptide selected from the group consisting of a capsid peptide of a phage, a phagemid, and a viroid, and
a third genetic construct encoding a therapeutic agent selected from the group consisting of at least one of a peptide, a DNA-based therapeutic and an RNA-based therapeutic, the therapeutic agent being adapted for treating an inflammatory disease,
the secretable delivery vehicle being adapted to deliver the therapeutic agent to a host mammal having the inflammatory disease.

* * * * *